United States Patent
Karlsson et al.

(10) Patent No.: US 8,309,529 B2
(45) Date of Patent: Nov. 13, 2012

(54) TUMOUR GROWTH INHIBITORY COMPOUNDS AND METHODS OF THEIR USE

(75) Inventors: Asa Karlsson, Sollentuna (SE); Oliver Von Stein, Upplands Vasby (SE); Arezou Zargari, Solna (SE); Nikolai Kouznetzov, Jarfalla (SE)

(73) Assignee: Index Pharmaceuticals AB, Stockholm (SE)

( * ) Notice: Subject to any disclaimer, the term of this patent is extended or adjusted under 35 U.S.C. 154(b) by 155 days.

(21) Appl. No.: 12/598,674

(22) PCT Filed: Apr. 30, 2008

(86) PCT No.: PCT/SE2008/050501
§ 371 (c)(1),
(2), (4) Date: Mar. 2, 2010

(87) PCT Pub. No.: WO2008/136748
PCT Pub. Date: Nov. 13, 2008

(65) Prior Publication Data
US 2010/0196356 A1    Aug. 5, 2010

Related U.S. Application Data

(60) Provisional application No. 60/927,584, filed on May 4, 2007.

(51) Int. Cl.
*A01N 43/04*    (2006.01)
*C07H 21/02*    (2006.01)
*C07H 21/04*    (2006.01)
*C12N 15/63*    (2006.01)

(52) U.S. Cl. ....... 514/44; 536/23.1; 536/24.33; 435/455

(58) Field of Classification Search .................... 514/44; 536/23.1, 24.33; 435/455
See application file for complete search history.

(56) References Cited

U.S. PATENT DOCUMENTS 6,194,388 B1     2/2001  Krieg et al.
7,691,997 B2 *   4/2010  Khvorova et al. ........... 536/24.5
2003/0026801 A1  2/2003  Weiner et al.

FOREIGN PATENT DOCUMENTS

WO    WO 95/35032 A1      12/1995
WO    WO 0061151     *    10/2000
WO    WO 2005/042018 A2    5/2005
WO    WO 2006135434 A2    12/2006

OTHER PUBLICATIONS

Karin et al., 2005, Geneseq Accession No. ADZ44604, computer printout pp. 6 and 7.*
Breton et al., 2003, Geneseq Accession No. ACH97195, computer printout pp. 22 and 23.*
Pettersson et al., 1997, Geneseq Accession No. AAV04132, computer printout pp. 4 and 5.*
Dias et al., 2000, EST Accession No. AW884118, computer printout, p. 13-14.*
Hehl et al., 2000, EST Accession No. N69710, computer printout, p. 61.*
Hillier et al., 1995, EST Accession No. R70211, computer printout, p. 62-63.*
Khvorova et al., 2010, US Patent No. 7,691,997 B2, computer printout, p. 6.*
Stephen et al., 2006, GenEmbl Accession No. FZ521449, computer printout, p. 47.*
Jahrsdorfer et al., "B-Cell Lymphomas Differ in their Responsiveness to CpG Oligodeoxynucleotides," *Clinical Cancer Research* (2005), 11:1490-1499.
Ponzio et al., "CpG Oligodeoxynucleotide-Induced Immunity Prevents Growth of Germinal Center-Derived B Lymphoma Cells," *International Immunopharmacology* (2006), 6:2057-2068, Elsevier B.V.
Reid et al., "CpG Stimulation of Precursor B-Lineage Acute Lymphoblastic Leukemia Induces a Distinct Change in Costimulatory Molecule Expression and Shifts Allogeneic T Cells toward a Th1 Response," *Blood* (2005), 105(9):3641-3647, The American Society of Hematology, Washington, D.C.
Warren et al, "CpG Oligodeoxynucleotides Enhance Monoclonal Antibody Therapy of a Murine Lymphoma", Clinical Lymphoma, 1(1):57-61 (2000).
Davila et al, "Generation of Antitumor Immunity by Cytotoxic T Lymphocyte Epitope Peptide Vaccination, CpG-oligodeoxynucleotide Adjuvant, and CTLA-4 Blockade", Cancer Research, 63:3281-3288 (2003).
Decker et al., "Sensitization of B-call chronic lymphocytic leukemia cells to recombinant immunotoxin by immunostimulatory phosphorothioate oligodeoxynucleotides", *Blood*, 99(4) 1320-1326, 2002.
Li, J. et al., "CpG in the Immunotherapy of B Cell Lymphoma in an Animal Model", *Immunothe*, 27(6) Abstract, 2004.

* cited by examiner

*Primary Examiner* — Shin-Lin Chen
(74) *Attorney, Agent, or Firm* — Porter Wright Morris & Arthur

(57) ABSTRACT

Specific CpG oligonucleotide sequences, when given subcutaneously and in particular when administered on a mucous membrane, e.g. intranasally, intravaginally, or rectally, have a profound effect on various human cancer forms as confirmed in vivo, in animal studies, and in vitro, in human PBMCs collected from blood from healthy subjects and from patients suffering from CLL or FL. The compounds are also preferably used in combination with a cancer therapy chosen among radiation treatment, hormone treatment, surgical intervention, chemotherapy, immunological therapies, photodynamic therapy, laser therapy, hyperthermia, cryotherapy, angiogenesis inhibition, or a combination of any of these, and is most preferably an immunological treatment and comprises the administration of an antibody to the patient.

16 Claims, 27 Drawing Sheets

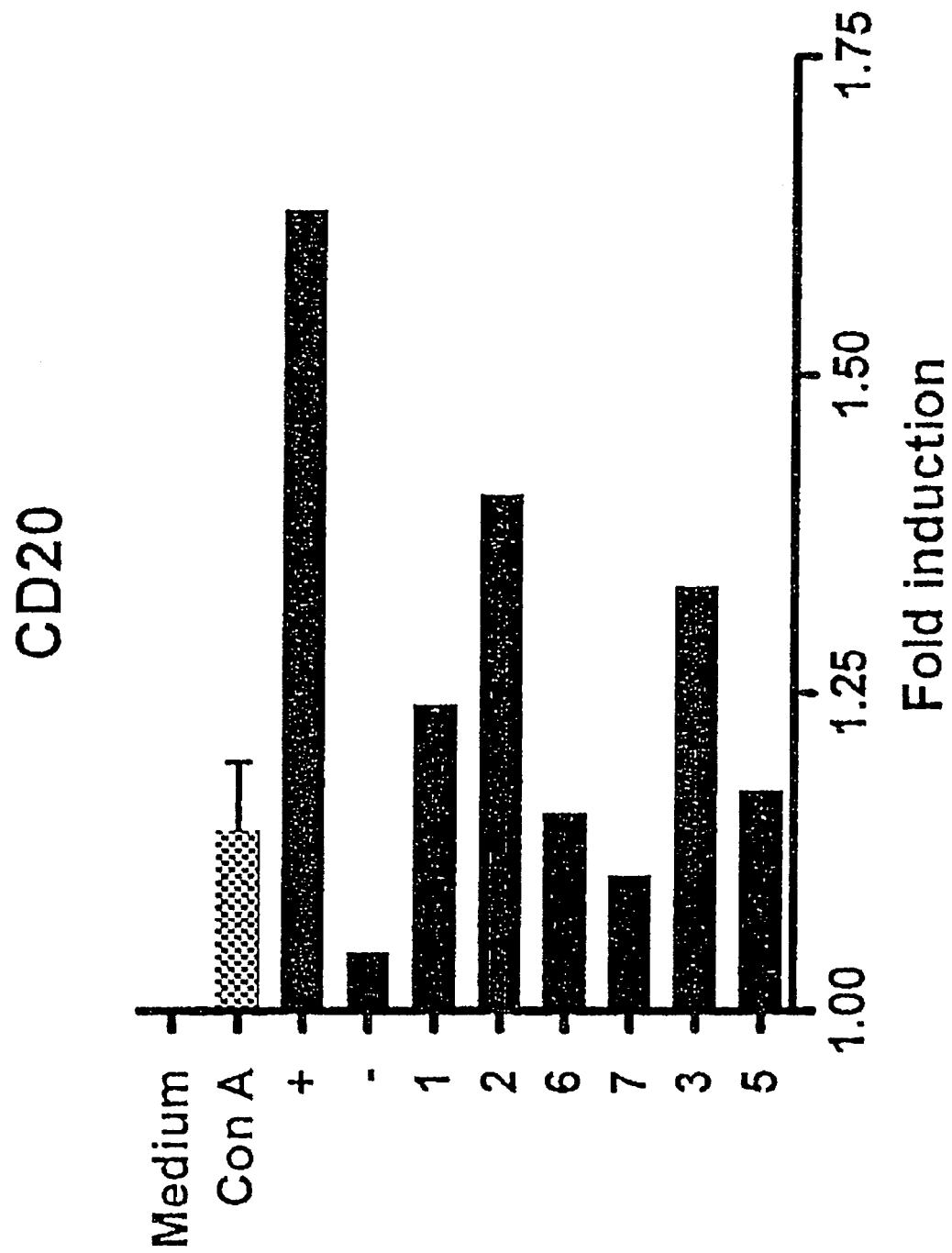

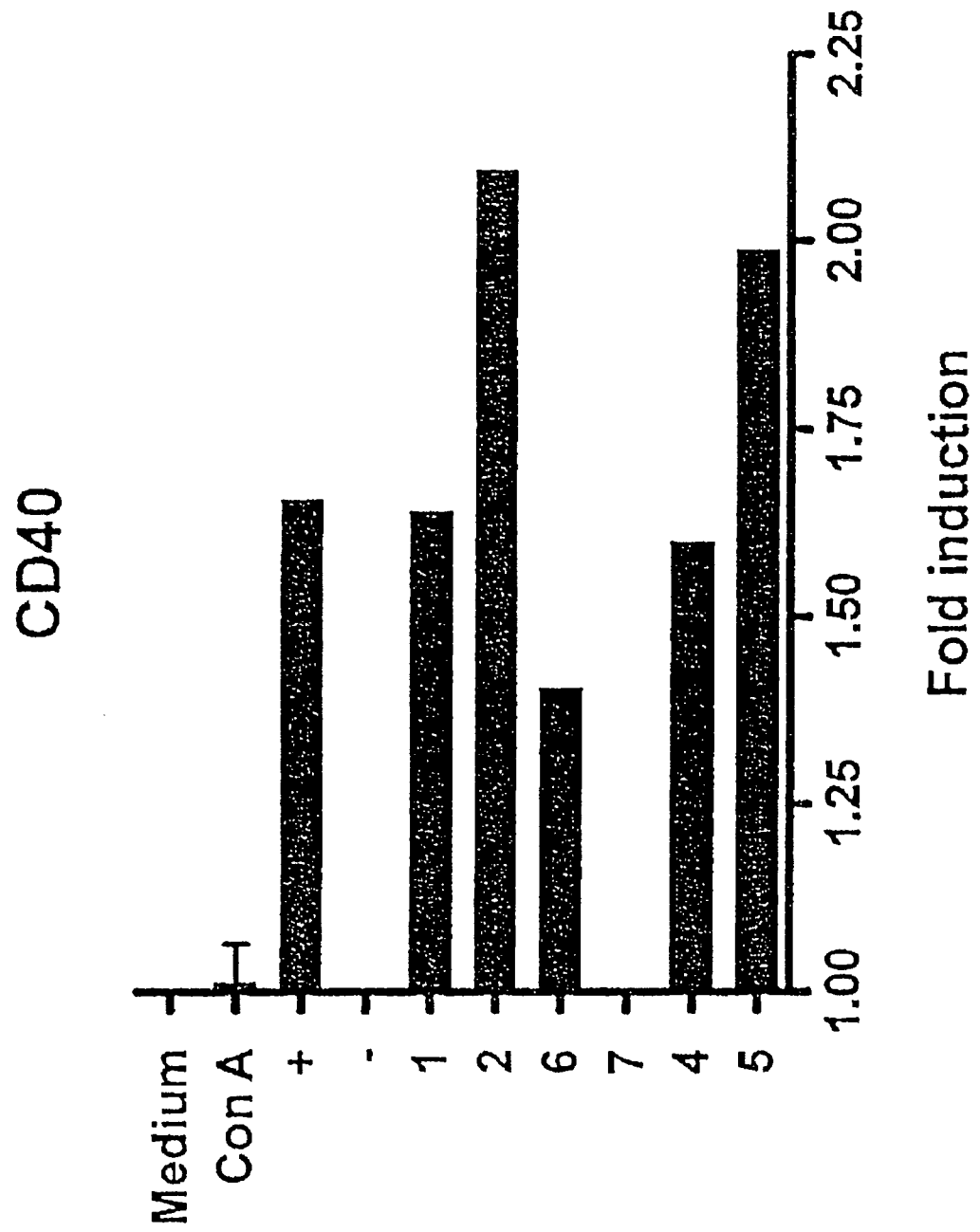

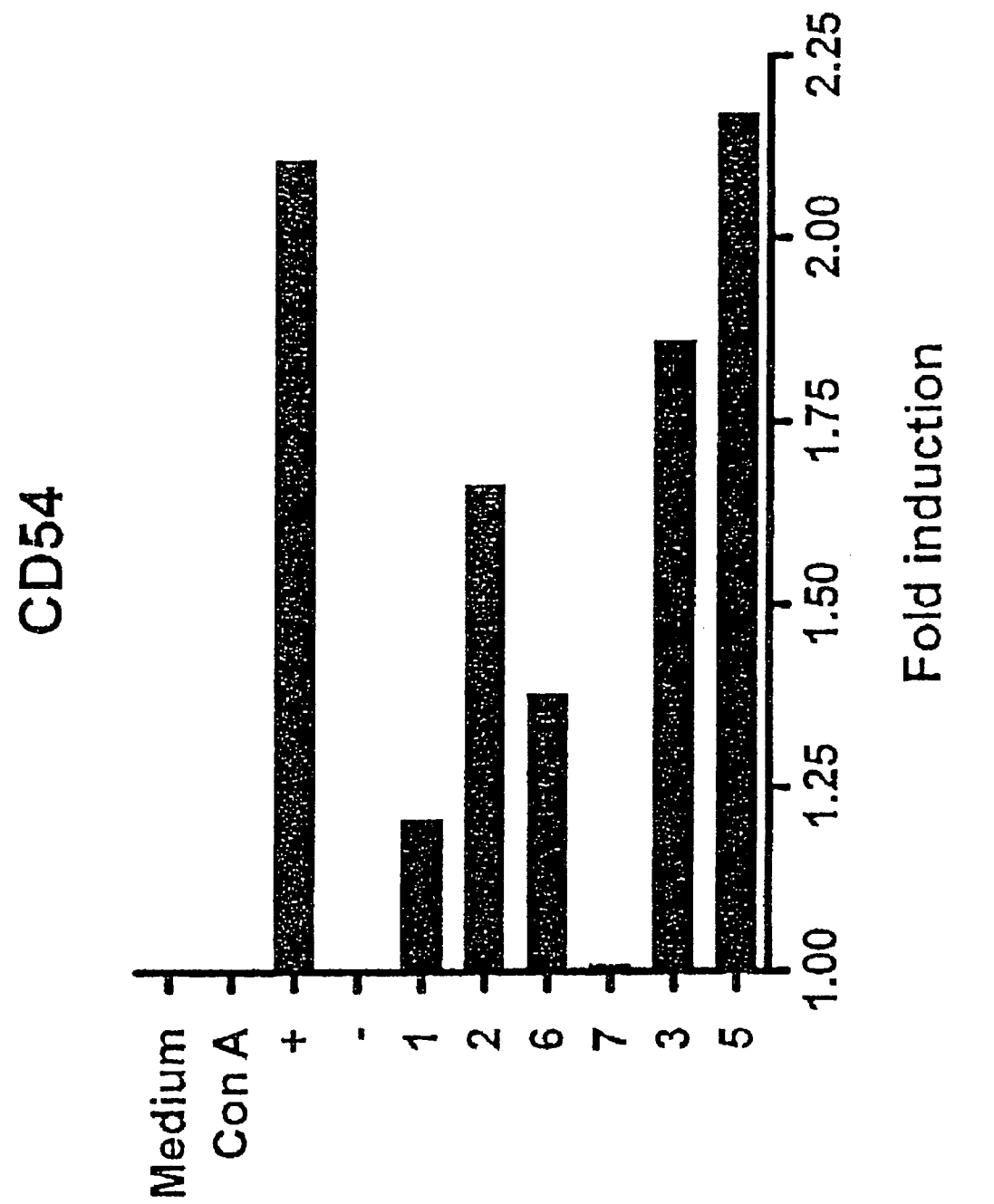

TUMOUR GROWTH INHIBITORY COMPOUNDS AND METHODS OF THEIR USE

CROSS REFERENCE TO RELATED APPLICATIONS

This application is a 35 USC §371 National Stage application of International Application No. PCT/SE2008/050501 filed Apr. 30, 2008, which claims the benefit under 35 USC §119(e) to U.S. Application Ser. No. 60/927,584 filed May 4, 2007. The disclosure of each of the prior applications is considered part of and is incorporated by reference in the disclosure of this application.

TECHNICAL FIELD

The present application relates to the field of medicine, and in particular to novel compounds and methods for their use in the treatment of cancer either alone or in combination with existing and future therapies.

BACKGROUND ART

Cancer treatment is entering an era of targeted approaches. One such approach is use of the immune system to recognize and eliminate malignant cells. Synthetic CpG oligonucleotides (CpG DNA) are a relatively new class of agents that have the ability to stimulate a potent, orchestrated tumour-specific immune response (KRIEG, A M. Lymphocyte activation by CpG dinucleotide motifs in prokaryotic DNA. Trends Microbiol. 1996, vol. 4, no. 2, p. 73-6; and KRIEG, A M, et al. Mechanisms and therapeutic applications of immune stimulatory CpG DNA. Pharmacol Ther. 1999, vol. 84, no. 2, p. 113-20.).

Recent studies demonstrate that at least three classes of CpG DNA sequences exist, each with different physical characteristics and biological effects. Preliminary studies in several animal models of cancer suggest that CpG DNA may have many uses in cancer immunotherapy. CpG DNA have the ability to induce tumour regression by activating innate immunity, enhancing antibody dependent cellular cytotoxicity, and serving as potent vaccine adjuvants that elicit a specific, protective immune response. Early clinical trials indicate that CpG DNA can be administered safely to humans, and studies are ongoing to understand how these agents may play a role in cancer immunotherapy (WOOLDRIDGE, J E, et al. CpG DNA and cancer immunotherapy: orchestrating the antitumour immune response. Curr Opin Oncol. 2003 November, vol. 15, no. 6, p. 440-5.)

An early patent (U.S. Pat. No. 6,498,147 B, THE SCRIPPS INSTITUTE, 2002 Dec. 24) presented antisense oligonucleotides and disclosed antisense inhibition of tumour cells in vitro, as well as an animal experiment showing antisense inhibition of tumour growth in vivo in syngenic C57B1/6 mice. The mice were treated with intraperitoneal injections of 40 mg/g sense and antisense oligodeoxynucleotides. Histologic analysis showed focal tumour necrosis followed by widespread segmental necrosis.

B-chronic lymphocytic leukemia (B-CLL) is the most common leukemia in the western world. B-CLL is a cancer of the white blood cells and bone marrow, characterized by uncontrolled proliferation and/or reduced cell death (apoptosis) of blood cells, specifically the B lymphocytes, and is the most widespread form of adult leukemia. Its incidence approaches 50 per 100,000 after the age of seventy. The leukemia usually has a protracted natural course of years and even decades, but eventually accelerates as the cells acquire sequential genetic defects. B-CLL differs from many other malignancies in that monoclonal B-CLL cells accumulate relentlessly, due to an abnormally prolonged life span, which likely is a consequence of altered interactions between defective B-CLL cells and their environment. Cytokines are essential factors in cell homeostasis and cell-cell dialogue, and are proposed to be critical in this milieu (CALIGARIS-CAPPIO et al., 1999, ROZMAN et al., 1995).

No common initial transforming event has been found for B-CLL. Chromosomal translocations, thought to occur mainly during the gene rearrangement process and common in other lymphoid malignancies, are rare in B-CLL. Karyotypic abnormalities tend to increase in frequency and number during the course of the disease. When translocations are found, they tend to result in genetic loss rather than in the formation of a fusion gene or over-expression of an oncogene. The most common genetic abnormalities in B-CLL are 13q deletions (50% of cases), 13q4 deletions (associated with an indolent course), trisomy 12 (12q13-15, with over-expression of the MDMQ oncoprotein which suppresses p53), and 1lq22-q23 deletions (20% of cases) (GAIDAN et al., 1991 et al., DOHNER et al., 1999).

B-CLL cells express surface molecules such as CD23 (low affinity receptor for IgE), CD25 (IL-2R α chain), and CD27 (co-stimulatory molecule), which in other settings indicate a state of activation. The expression and association of several proteins tightly regulate the process of apoptosis. The relative balance of these proteins controls cell life span. Genes responsible for this system include the BCL-2 family, the tumour necrosis factor receptor and genes such as Myc and p53 (OSORIO et al., 1999). All the death pathways promoted by these genes appear to have a common 'demolition" cascade, represented by the protease family of the caspases. B-CLL cells consistently express high levels of products of the anti-apoptosis members of the BCL-2 family (bad-2, bcl-n, bax), while the Bcl-2 function inhibitor Bcl-6 is markedly reduced. The mechanism involved in over-expression of Bcl-2 is currently unclear. The leukemic cells of B-CLL are negative or weakly positive for Fas. They generally remain resistant to anti-Fas antibody mediated death even after stimulation induced Fas expression. In rare sensitive cases, cell death occurs independently of Bcl-2 expression by a mechanism still uncharacterized. It would appear that Bcl-2 over-expression and the Fas pathway are mechanisms involved in the pathophysiology of B-CLL but not necessarily critical causative events. Mediators including cytokines are likely to link the initial etiologic factor with the terminal pathways of apoptosis.

Most B-CLL cells are the in G0 phase of the cell cycle and can not be induced to enter the proliferative phase by conventional methods such as concanavalin-A, phorbolesters, or receptor cross-linking, which induce the proliferation of normal lymphocytes. Only a small subset of cells appears to enlarge the clonal population in response to an unknown promoting signal. Proliferation promoting cytokines may provide this stimulus in vivo (DANCESCU et al, 1992).

B-CLL cells accumulate at the expense of the normal B-cell pool. Total T-cells on the other hand, are usually increased. The bone marrow T-lymphocytes are predominantly CD4+ cells as seen in autoimmune disorders such as rheumatoid arthritis and sarcoidosis. There is frequently a Th2 predominant cytokine phenotype in peripheral blood. Abnormalities in the TCR repertoire have been reported also. Reports indicate that T-lymphocytes and stromal cells may have a key role in supporting an environment capable of perpetuating the life span of the B-CLL cells. Both the malignant cells and their T-cell entourage express a vanity of surface molecules and their receptors: CD5 and its ligand CD72, CD27 and CD70. These findings open various possibilities of mutual interaction which could result directly or indirectly (cytokines) in cell self-preservation. Such lengthy survival would, in turn increase chances for accumulation of gene mutations and genetic instability, which favours disease progression through dysregulation of cell cycle check-points, and resistance to cytotoxic therapy (KLEIN et al., 2000).

The symbiotic interaction between B-CLL cells and their environment is almost certainly mediated by the secretion of cytokines and modulated by adhesion molecules. Investigation of cytokine involvement in B-CLL has generated a substantial body of data supporting or disproving various cytokines as mediators of proliferation and prolonged life span in this leukemia. Cytokine production investigations have demonstrated reverse-transcription polymerase chain reaction signals for IL1, IL2, IL3, IL4, IL5, IL7, TNF-β, and TNF-α (PISTOIA et al., 1997). These findings have been contradicted by other studies which showed negative results for IL4, IL3 and IL6 (TANGYE et al., 1999). In contrast, TGF-β, as well as IL10 secretion, has been show in normal B-lymphocytes. No other cytokine production has been reported to be constitutive for these cells.

Immunotherapy of cancer has been explored for over a century, but it is only in the last decade that various antibody-based products have been introduced into the management of patients with diverse forms of cancer. At present, this is one of the most active areas of clinical research, with eight therapeutic products already approved in oncology. Antibodies against tumour-associated markers have been a part of medical practice in immunohistology and in vitro immunoassays for several decades, and are now becoming increasingly recognized as important biological agents for the detection and treatment of cancer (STROME et al., 2007). Molecular engineering has improved the prospects for such antibody-based therapeutics, resulting in different constructs and humanized or human antibodies that can be frequently administered.

CD20 is variably expressed on the surface of B-cells in CLL patients with some patient's B-cells expressing very low levels of CD20 antigen. CD20 (human B-lymphocyte restricted differentiation antigen), is a hydrophobic transmembrane protein with a molecular weight of approximately 35 kD located on pre-B and mature B lymphocytes. The antigen is also expressed on more than 90% of B-cells in non Hodgkin's lymphomas (NHL), but is not found on hematopoietic stem cells, pro B cells, normal plasma cells or other normal tissues. CD20 regulates an early step(s) in the activation process for cell cycle initiation and differentiation, and possibly functions as a calcium ion channel. CD20 is not shed from the cell surface and does not internalize upon antibody binding. Free CD20 antigen is not found in the circulation (PESCOVITZ, 2006).

The anti-CD20 antibody Rituximab, which is a genetically engineered chimeric murine/human monoclonal antibody directed against human CD20 (Rituxan® or MabThera®, from Genentech, Inc., South San Francisco, Calif., U.S.) is used for the treatment of patients with relapsed or refractory low-grade or follicular, CD20 positive, B-cell non-Hodgkin's lymphoma and B-CLL. Rituximab works by recruiting the body's natural defense to attack and kill the B-cell to which it binds via the CD20 antigen. In vitro mechanism of action studies have demonstrated that Rituximab binds human complement and lyses lymphoid B-cell lines through complement-dependent cytotoxicity (CDC) (REFF et al., 1994). Additionally, it has significant activity in assays for antibody-dependent cellular cytotoxicity (ADCC). In vivo preclinical studies have shown that Rituximab depletes B-cells from the peripheral blood, lymph nodes, and bone marrow of cynomolgus monkeys, presumably through complement and cell-mediated processes (REFF et al., 1994). While Rituximab has been used with some success in CLL patients, analysis of CLL patients shows that the density of CD20 on the surface of B-CLL cells is rather variable with some patient's B cells expressing very low levels of CD20 antigen. The typical treatment for B-cell malignancies, besides Rituximab, is the administration of radiation therapy and chemotherapeutic agents. In the case of CLL, conventional external radiation therapy will be used to destroy malignant cells. However, side effects are a limiting factor in this treatment. Another widely used treatment for haematological malignancies is chemotherapy. Combination chemotherapy has some success in reaching partial or complete remissions. Unfortunately, these remissions obtained through chemotherapy are often not durable.

Conversely, CD23 expression has been found to be consistently present at higher levels in B-CLL. The CD23 leukocyte differentiation antigen is a 45 kD type II transmembrane glycoprotein expressed on several haematopoietic lineage cells, which function as a low affinity receptor for IgE (FcγRII) (PATHAN et al., 2008). It is a member of the C-type lectin family and contains an α-helical coiled-coil stalk between the extracellular lectin binding domain and the transmembrane region. The stalk structure is believed to contribute to the oligomerization of membrane-bound CD23 to a trimer during binding to its ligand (for example, IgE). Upon proteolysis, the membrane bound CD23 gives rise to several soluble CD23 (sCD23) molecular weight species (37 kD, 29 kD and 16 kD). In addition to being involved in regulating the production of IgE, CD23 has also been speculated to promote survival of germinal center B cells. The expression of CD23 is highly up-regulated in normal activated follicular B cells and in B-CLL cells.

Lumiliximab is a monoclonal chimeric anti-CD23 antibody (from Biogen Idec, currently undergoing clinical trials) that harbours macaque variable regions and human constant regions (IgG1, κ) and was originally developed to inhibit the production of IgE by activated human blood B-cells. It is now in a Phase III trial for use in B-CLL patients. In vitro studies have shown that Lumiliximab induces caspase dependent apoptosis in B-CLL cells through the mitochondrial death pathway (PATHAN et al., 2008). Thus, it seems to induce apoptosis of tumour cells through a mechanism different from Rituximab.

Several other antibodies have recently been approved for the treatment of cancer. Alemtuzumab (Campath® or MabCampath®, an anti-CD52 from Ilex Pharmaceuticals) (KEATING et al., 2002) was approved in 2001 for the treatment of CLL. Bevacizumab (Avastin®, Genentech, Inc., South San Francisco, Calif.) is a humanized IgG1 mAb directed against vascular endothelial growth factor (VEGF) used in treatment of colorectal cancer, small cell lung cancer and breast cancer. Trastuzumab (Herceptin® from Roche) is a humanized IgG1 mAb that is effective against metastatic breast cancer tumours over-expressing the HER-2 target (STROME et al., 2007).

In order to make antibody drugs more efficient, an up-regulation of the specific antigen targets on the surface of tumour cells might be helpful. One way of obtaining such an effect could be to stimulate the cells with immunomodulatory oligonucleotides. Immune stimulatory effects can be obtained through the use of synthetic DNA-based oligodeoxynucleotides (ODN) containing unmethylated CpG motifs.

Such CpG ODN have highly immunostimulatory effects on human and murine leukocytes, inducing B cell proliferation; cytokine and immunoglobulin secretion; natural killer (NK) cell lytic activity and IFN-gamma secretion; and activation of dendritic cells (DCs) and other antigen presenting cells to express co-stimulatory molecules and secrete cytokines, especially the Th1-like cytokines that are important in promoting the development of Th1-like T cell responses (KRIEG et al, 1995). The increase in receptor density by CpG-ODNs could be mediated through a direct effect of the oligonucleotides on the cells, or through the induction of cytokines. An increase in antigen density or an increase in the population of cells expressing the target receptors would enable the antibodies to kill the tumour cells more efficiently, either through enhancing antibody-dependent cellular cytotoxicity (ADCC) or complement-dependent cytotoxicity (CDC). WO 95/35032 concerns oligonucleotides (antisense) which hybridize to NF-kB mRNA and methods of using these to suppress processes which depend upon activation of NF-kB. Such processes are typically associated with such disorders as those mediated by immune or cytokine responses (for example, septic or non-septic shock) as well as those disorders induced by infectious agents such as retroviruses, more specifically, HIV and HTLV.

There are indications that the CpG motif alone is not accountable for the efficacy of the oligonucleotides. There are even indications that this motif is not necessary for the desired function.

Regardless of the considerable effort spent on developing oligonucleotide based therapeutic approaches to cancer, and the occasional success reported so far, there still remains a need for new compounds and modes of administration, exhibiting improved efficacy and minimal or no side effects.

SUMMARY OF THE INVENTION

The present inventors have surprisingly found that specific oligonucleotide sequences when given subcutaneously or in particular when administered topically on a mucous membrane, e.g. orally, pulmonary, intranasally, rectally, or intravaginally, have a profound effect on various human cancer forms as confirmed in vivo, in animal studies, and in vitro, using PBMCs from CLL patients and healthy subjects.

Further, novel sequences have been developed and tested, showing pronounced therapeutic effects either alone or in combination with other treatments. The oligonucleotides are used to induce apoptosis, to activate NK-cells, inhibit neutrophil migration, and in particular to increase the expression of cell surface receptors. The inventive oligonucleotides can be used in combination with immunological approaches to treat cancer, e.g. monoclonal antibodies directed to specific receptors. Embodiments of the invention are defined in the attached claims, incorporated herein by reference.

BRIEF DESCRIPTION OF THE DRAWINGS

The invention will be described in closer detail in the following description, non-limiting examples and claims, with reference to the attached drawings in which

FIG. 10 consists of three bar diagrams (10 a, b and c) showing the effect on the expression of B-cell proliferation markers CD20, CD40 and CD54 in a human B-cell lymphoma model in vitro, following administration of the compounds according to SEQ ID NO. 1-7;

DESCRIPTION

Figure 1:
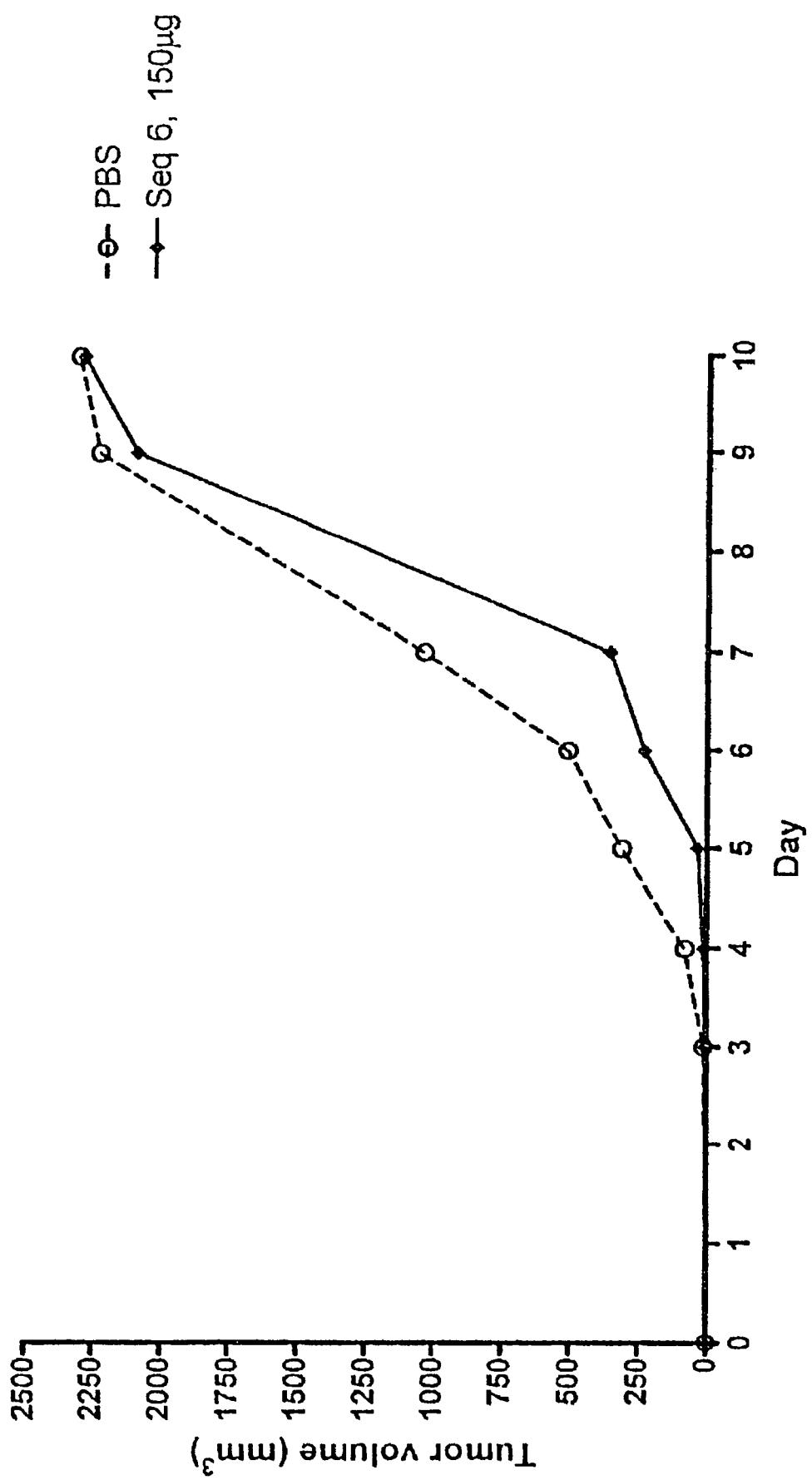
FIG. 1 is a graph showing tumour growth measured as tumour volume ($mm^3$) over time for mice with induced subcutaneous RMA lymphoma, following subcutaneous administration of 150 µg of the substance of SEQ ID NO. 6, compared to control (PBS)

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" also include plural referents unless the context clearly dictates otherwise. Thus, for example, reference to "a sequence" includes more than one such sequence, and the like.

Further, the term "about" is used to indicate a deviation of +/−2% of the given value, preferably +/−5% and most preferably +/−10% of the numeric values, when applicable.

The term "cancer" is meant to mean any malignant neoplastic disease, i.e. any malignant growth or tumour caused by abnormal and uncontrolled cell division. The term "cancer" is in particular meant to include both solid, localized tumours, as exemplified in the animal experiments included in the present description, and non-solid cancer forms, such as but not limited to chronic lymphocytic leukaemia (CLL) and follicular lymphoma (FL), two forms of leukaemia investigated in the examples.

The present inventors have identified novel oligonucleotide sequences capable at least one of the following: induction of apoptosis, activation of NK-cells, inhibition of neutrophils, and up-regulation of the expression of specific cell surface markers. The inventors have also made available novel methods of therapy, and surprisingly found that a reduction in dose (from 150 µg to 50 µg) significantly improved the response in subcutaneous administration, and that application on a mucous membrane, here tested in the form of nasal administration, provided an equally effective way of administration.

Without wishing to be bound to any theory, the present inventors contemplate that the oligonucleotide sequences presented herein are capable of inhibiting migration of cells, in particular neutrophils, to the site of the tumour, thus inhibiting the growth of the tumour. Further, the experiments on human cell lines in vitro indicate that the oligonucleotides according to the invention are capable of both reducing growth and inducing apoptosis.

Contrary to the theory that impairment of neutrophil migration is an effect of cancer, making the individual susceptible to infections, the present inventors contemplate that tumours to some extent benefit from, or are capable of using the defense system of the body, i.a. the inflammatory reactions, to their advantage. The inventive compounds SEQ ID NO 1-5 and 8-9 presented in Table 1 offer a possibility to inhibit such mechanisms.

The inventors also surprisingly show that the compounds are capable of eliciting or increasing the expression of cell surface markers, here illustrated by CD20, CD23, CD25, CD40, CD54, CD69, CD80, and CD86.

The inventors therefore make available, as one embodiment of the invention, compounds and methods for the treatment of cancer, wherein the inventive compounds presented in Table 1 are used either alone; to increase apoptosis, to activate NK-cells, to up-regulate the expression of one or more of the cell surface markers CD20, CD23, CD25, CD40, CD54, CD69, CD80, and CD86; or in combination with an anti-tumour therapy chosen among surgical removal of the tumour, radiation treatment, hormone treatment, surgical intervention, chemotherapy, immunological therapies, photodynamic therapy, laser therapy, hyperthermia, cryotherapy, angiogenesis inhibition, or a combination of any of these. Most preferably said anti-tumour treatment is an immunological treatment and comprises the administration of an antibody to the patient.

Examples of presently available antibodies include, but are not limited to, Rituximab (Rituxan®, MabThera®), Lumiliximab, Alentuzumab (Campath®, MabCampath®), Bevacizumab (Avastin®), and Trastuzumab (Herceptin®).

When given in combination with an anti-tumour therapy, the inventive compounds are preferably administered in advance of the anti-tumour therapy, preferably 30 min, 1 hour, 2 hours, 3 hours, 6 hours or 12 hours in advance of the therapy. When given in combination with an immunological therapy, and in particular a therapy involving the administration of an antibody, the inventive compound is preferably administered before the administration of the antibody to the patient, and most preferably sufficiently before in order to allow for the up-regulation of cell surface molecule or cell surface marker towards which the specific antibody is targeted.

The invention makes available specific nucleotides, i.e. the isolated oligonucleotide sequences according to any one of SEQ ID NO 1-5 and 8-9. See Table 1.

TABLE 1

Sequence information
Table 1

| SEQ ID No. | Sequence (5'-3') | IDX-No |
|---|---|---|
| 1 | C*C*G*GGGTCGCAGCTGAGCCCA*C*G*G | 0011 |
| 2 | A*T*C*GTCTGCCATGGTGAA*G*A*T | 0013 |
| 3 | T*C*G*TCGTTCTGCCATCGTC*G*T*T | s0022 |
| 4 | G*G*G*GTCGTCTG*C*G*G | s0052 |
| 5 | G*A*T*CGTCCGTCGG*G*G*G | s0058 |
| 6 | G*G*A*ACAGTTCGTCCAT*G*G*C | 0150 |
| 7 | G*G*G*GAACAGTTCGTCCAT*G*G*C | 0955 |
| 8 | T*C*G*TCGTTCGGCCGATCG*T*C*C | 9038 |
| 9 | T*C*G*TTCGTCTGCTTGTTC*G*T*C | 9071 |

Note:
*denotes phosphothiolation

The above sequences SEQ ID NO 1-5 and 8-9 have been synthesized by the inventors. SEQ ID NO 2 corresponds to a sequence published in WO 95/35032. SEQ ID NO 6 was published for the first time in U.S. Pat. No. 6,498,147, and SEQ ID NO 7 has been published i.a. by SOKOLOSKI, J A, et al. Antisense oligonucleotides to the p65 subunit of NF-kB block CD11b expression and alter adhesion properties of differentiated HL-60 granulocytes. Blood. 15 Jul. 1993, vol. 82, no. 2, p. 625-632.

The oligonucleotide sequence according to any one of SEQ ID NO 3, 1, 4, 5, 6, 8 and 9 may comprise at least one nucleotide having a phosphate backbone modification. Said phosphate backbone modification is preferably a phosphorothioate or phosphorodithioate modification.

The present invention also comprises the use of an isolated oligonucleotide sequence according to any one of SEQ ID NO 3, 1, 4, 5, 6, 8 and 9 for the manufacture of a medicament for the treatment of cancer, in particular for the treatment of cancer through inhibition of tumour growth, e.g. through the inhibition of neutrophil migration to the site of the tumour.

According to a preferred embodiment, the medicament is administered nasally in a dose effective to achieve at least one of up-regulation of a cell surface marker, induction of apoptosis, activation of NK-cells, and inhibition of neutrophil migration in the treatment of cancer. Said dose is preferably in the interval of about 1 to about 100 µg for the treatment of cancer.

Correspondingly, the invention also comprises the use of an isolated oligonucleotide sequence according to any one of SEQ ID NO 3, 1, 4, 5, 6, 8 and 9 for the manufacture of a medicament for subcutaneous administration in a dose effective to achieve at least one of up-regulation of a cell surface marker, induction of apoptosis, activation of NK-cells, and inhibition of neutrophil migration in the treatment of cancer. Said dose is preferably in the interval of about 1 to about 100 µg for the treatment of cancer.

One embodiment of the invention comprises the use as defined above, wherein an anti-tumour treatment is administered before, after or essentially simultaneously with the administration of said oligonucleotide. This anti-tumour treatment is chosen among radiation treatment, hormone treatment, surgical intervention, chemotherapy, immunological therapy, photodynamic therapy, laser therapy, hyperthermia, cryotherapy, angiogenesis inhibition, or a combination of any of these.

The anti-tumour treatment is preferably an immunological therapy involving the administration of an antibody to the patient.

In either one of the above embodiments of the invention, said oligonucleotide is administered in a dose effective to elicit or increase or up-regulate the expression of at least one cell surface molecule or cell surface marker, in particular a cell surface marker chosen among CD20, CD23, CD25, CD40, CD524, CD69, CD80, and CD86.

A skilled person is well aware of the fact that there are numerous approaches to the treatment of cancer. It is characteristic for the battle against cancer that several therapies are used, depending on the type of cancer, its location and state of progression, and the condition of the patient. It is frequently so that several therapies are used subsequently, or in combination. While some therapies such as surgical intervention, radiation therapy and chemotherapy have been practiced for many decades, others have been recently conceived and many are still in experimental use. Naturally new approaches are constantly being developed, and it is conceived that the oligonucleotides, their use and methods of treatment according to the present invention, will find utility also in combination with future treatments. The inventors presently believe that the inventive oligonucleotides, their use and methods of treatment would be useful in combination with the following anti-tumour treatments, however without wishing to be limited to the same; radiation treatment, hormone treatment, surgical intervention, chemotherapy, immunological therapy, photodynamic therapy, laser therapy, hyperthermia, cryotherapy, angiogenesis inhibition, or a combination of any of these.

The anti-tumour treatment is preferably an immunological therapy involving the administration of an antibody to the patient.

The oligonucleotide is administered in a therapeutically effective dose. The definition of a "therapeutically effective dose" is dependent on the disease and treatment setting, a "therapeutically effective dose" being a dose which alone or in combination with other treatments results in a measurable improvement of the patient's condition.

Effective amounts of oligonucleotides for treating cancer would broadly range between about 0.01 µg to about 100 µg per kg of body weight, preferably about 0.1 µg to about 10 µg, and most preferably about 1 µg to about 5 µg per kg of body weight of a recipient mammal. The oligonucleotide may be administered in a single dose or in repeated doses. The currently most preferred embodiment entails one single dose of the nucleotide according to the invention, administered to a mucous membrane, e.g. given intranasally, orally, rectally or intravaginally in an amount of 50 µg.

The nucleotides according to the invention can be delivered subcutaneously or topically on a mucous membrane. The term "topically on a mucous membrane" includes oral, pulmonary, rectal, vaginal, and nasal administration. According to one embodiment of the invention, the nucleotides are delivered intranasally. It is well known that the accessibility and vascular structure of the nose make nasal drug delivery an attractive method for delivering both small molecule drugs and biologics, systemically as well as across the blood-brain barrier to the CNS. The nucleotides can be delivered in any suitable formulation, such as suitable aqueous buffers, for example but not limited to phosphate buffered saline (PBS). It is contemplated that the nucleotides are administered in a suitable formulation, designed to increase adhesion to the mucous membrane, such as suitable gel-forming polymers, e.g. chitosan etc; a formulation enhancing the cell uptake of the nucleotides, such as a lipophilic delivery vehicle, liposomes or micelles; or both.

There are several methods and devices available for nasal administration; single or multi-dosing of both liquid and powder formulations, with either topical or systemic action. Using appropriate devices or administration techniques, it is possible to target the olfactory bulb region for delivery to the CNS. The present invention is not limited to particular methods or devices for administering the nucleotides to the nasal mucous membrane. The initial animal studies have shown that simple instillation by pipette works satisfactorily, although for human use, devices for reliable single or multi dose administration would be preferred.

According to another embodiment of the invention, the oligonucleotides are administered to the mucous membrane of the colon through rectal instillation, e.g. in the form of an aqueous enema comprising the oligonucleotides suspended in a suitable buffer.

According to another embodiment of the invention, the oligonucleotides are administered to the mucous membrane of the lungs or the airways through inhalation of an aerosol, comprising the oligonucleotides suspended in a suitable buffer, or by performing a lavage, also comprising the oligonucleotides suspended in a suitable buffer.

According to yet another embodiment of the invention, the oligonucleotides are administered to the mucous membrane of the urogenital tract, such as the urethra, the vagina etc through application of a solution, a buffer, a gel, salve, paste or the like, comprising the oligonucleotides suspended in a suitable vehicle.

Although the effect from application to the nasal mucosa has been shown to be systemic, it is contemplated that application to other locations, such as the mucous membranes of the urogenital tract, the airways or the intestines, is more suitable for the treatment of tumours located in these organs or in the vicinity thereof.

The invention finds utility in the treatment of cancer, as supported by the in vivo and in vitro data presented in the experimental section and illustrated in the attached figures.

The embodiments of the invention have many advantages. So far, the administration of an oligonucleotide in the doses defined by the inventors has not elicited any noticeable side-effects. Further, the mucosal administration is easy, fast, and painless, and surprisingly results in a systemic effect. The influence on the conditions at the site of the tumour, e.g. through inhibition of neutrophil migration to the tumour site is believed to be one, but not the only, factor responsible for the reduction of growth and induction of apoptosis seen in the experiments. It is held that this effect, either alone, or in combination with existing and future anti-cancer treatments, offers a promising approach to battling cancer.

EXAMPLES

1. Animal Experiments

The effect of subcutaneous growth of RMA lymphoma cells was investigated in vivo, in syngeneic C57BL/6 (B6) mice following administration of oligonucleotides. The objective of the study was to investigate the tumour growth inhibitory effect of different oligonucleotides in an experimental murine model of subcutaneous tumour growth. It is known that experimental subcutaneous tumours can be induced by inoculation of recipient B6 mice with in vivo maintained RMA tumour cells.

The study involved 10 groups of eight C57BL/6 (B6) mice each, a total of 80 mice.
1.1 Test Systems
Tumour Cell Type and Induction Induction of a subcutaneous tumour in mice is achieved by inoculation of a cell suspension ($10^3$) of in vivo-grown Raucher virus-induced lymphoma cells (RMA) into the right flank of the animal.
Test Article Formulation and Preparation The oligonucleotides to be investigated were supplied and delivered by Index Pharmaceuticals AB, Stockholm, Sweden, at room temperature in "ready to use" concentrations (2.5-1.25 µg/µL) and kept at −20° C. until the day of instillation.
1.2 Animal Material and Conditions
Species, Strain and Supplier The mice used are inbred C57BL/6/By mice obtained through in house breeding at MTC, Karolinska Institutet, Stockholm, Sweden.
Specifications The weight of the mice was approximately 20 grams. 80 mice divided into 10 experimental groups were used in the experiments. The mice were handled according to normal routines for immunocompetent animals at the MTC animal facility, which included housing in open cages, handling with gloves on open benches.
Environment The mice were maintained in standard open cages of M3 type (w:l:h=25:40:16 cm). The cages were housed in open racks under continuous air flow behind plastic curtains. Standard bedding was purchased from Scanbur-BK, Sollentuna, Sweden. Bedding was changed once a week. The temperature in the animal rooms was maintained in the interval of 18° C.-22° C. and controlled via the ambient ventilation system in the laboratory. The light cycle was 12-hour dark and 12-hour light (lights on 06.00).
Diet and Water The mice were given normal mouse diet purchased from Scanbur-BK, Sollentuna, Sweden. Water bottles were refilled when necessary during acclimatization and experimentation. Diet and water was available ad libitum.
1.3 Pre-Experimental Procedures
Acclimatization and Health Procedures The mice were imported to the laboratory at least 5 days before the start up of the experimental procedure in order to assure proper acclimatization.
Random Allocation to Treatment Groups After inspection and health clearance, the mice were randomly picked from the crates, individually marked by ear marks, and allocated into the experimental groups.
1.4. Experimental Procedures/Experimental Design
Set-Up The experimental procedures were initiated at least 5 days after arrival of the mice to the research unit. The groups were randomly assigned and treated according to the experimental protocol.
Experimental Procedures In brief, the experiment comprised the following actions: RMA tumour cells were grown as an ascites tumour in B6 mice to provide a source of tumour cells adapted to in vivo growth. After retrieval, a low dose of RMA tumour cells was inoculated into the right flank in recipient B6/By mice. A tumour cell dose of $10^3$ cells was be used for this experiment.

After tumour cell inoculation, all mice were monitored twice per week by palpation at the site of injection. At the first signs of tumour growth in any mouse, the mice were subdivided into groups and given 3 doses (100 µl) at one dose of the test substances every three days. The test substances were given subcutaneously in the left flank of the animals. In one group of mice, the test substance was also administered intranasally. For this group 50 μg (40 μl) of the substance was administered.

Control animals received a total of 3 doses, divided at one dose every three days of the vehicle only (PBS). The number of recipient mice were eight per experimental group, for a total of 10 groups, i.e. a total of 80 mice. The mice were continuously monitored and the growths of the subcutaneous tumours are measured and expressed as cancer mass volumes.

Treatment of Subcutaneous RMA Tumours

Animals received in total three subcutaneous injections (100 μL) of the oligonucleotides in the left flank, one injection every three days starting at the time point of the first signs of measurable tumour growth. Tumour size was measured using a caliper and expressed as cancer mass volume (mm$^3$).

Evaluation of Tumour Growth Rate

Each mouse is followed by manual palpation. As soon as a tumour appears, its size will be measured using a caliper every day.

Terminal Procedures

The tumour-bearing animals were sacrificed when the size of its growing tumour reached 1500 mm$^3$. Any animal not developing a tumour was monitored for a maximum of two months, at which point the mouse was sacrificed.

Mouse Tumour Specimen Collection

The tumour was excised using gloves, sterile scalpel and forceps after all measurements have been made. A portion of tumour mass, about 400-500 mg, was cut out, sliced with a sterile scalpel and transferred into storage solution into a prepared labelled Eppendorf tube. The tube was closed tightly and the contents mixed by inversion 5-6 times. The collected samples were stored at 4° C. until analyzed.

1.5 Results

Figure 2:
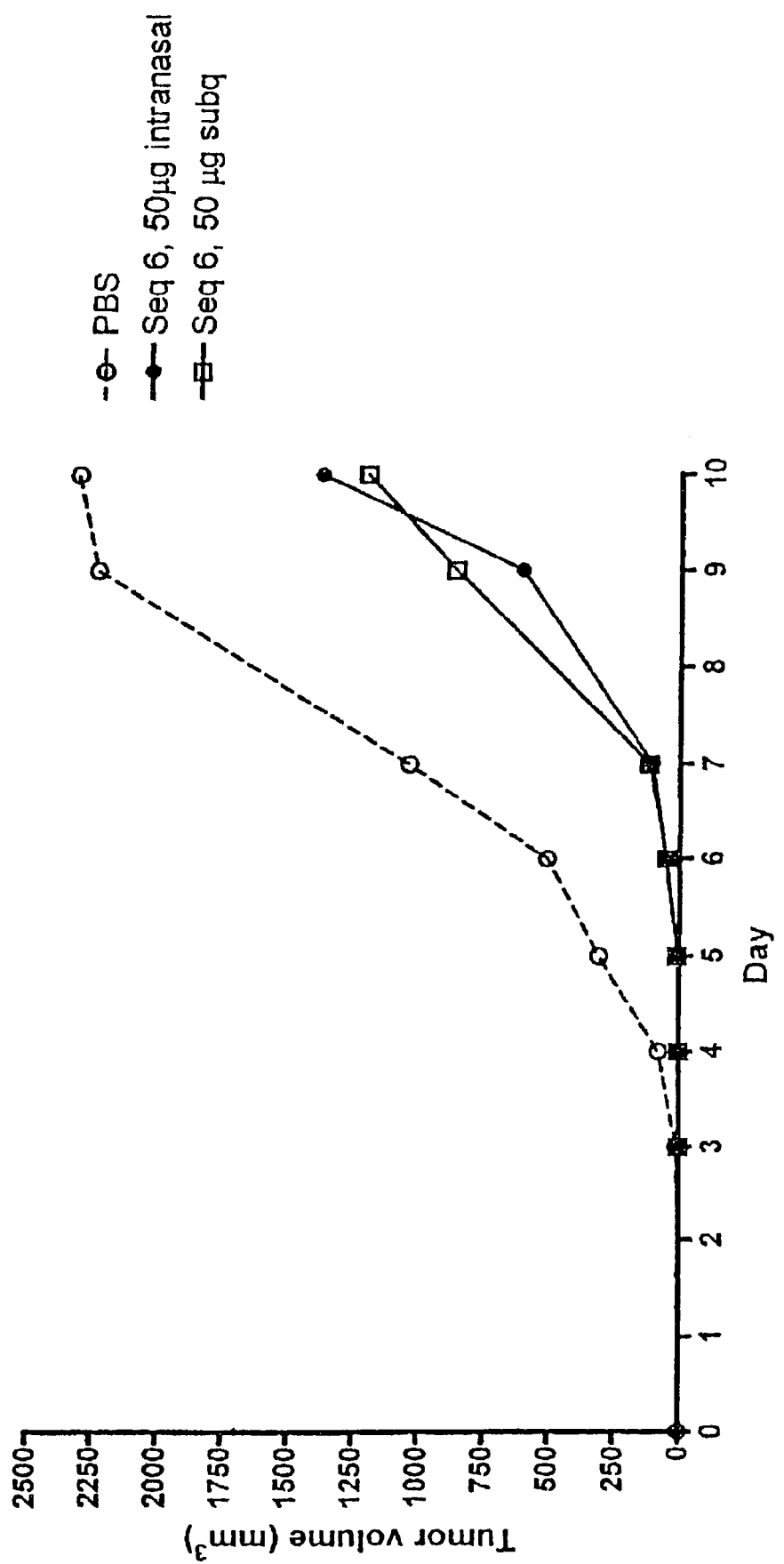
FIG. 2 is a graph as FIG. 1, here showing a comparison between the substance of SEQ ID NO. 6, given subcutaneously (50 µg bolus) and intranasally (50 µg), compared to control (PBS)
Figure 3:
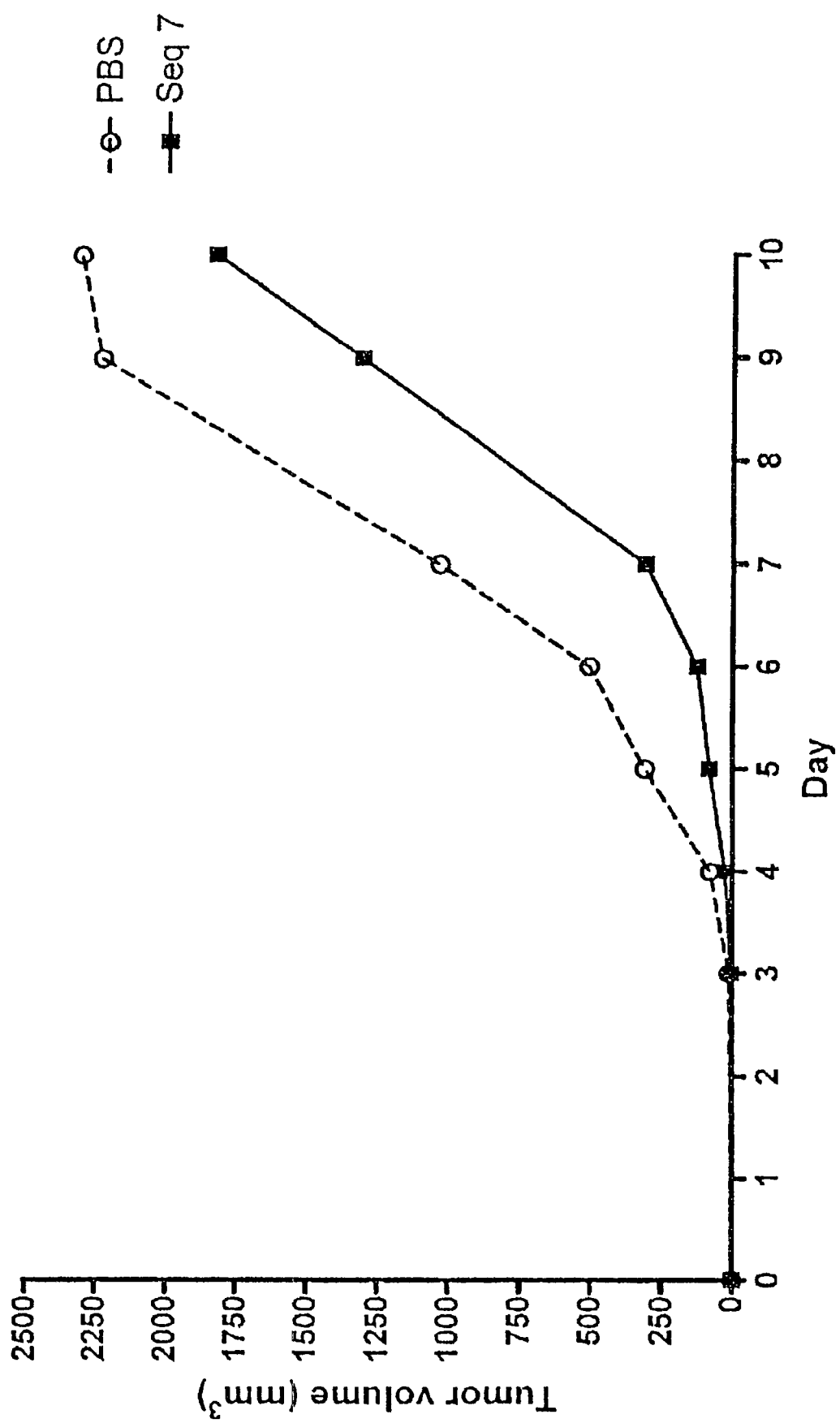
FIG. 3 is a graph showing tumour growth measured as tumour volume ($mm^3$) over time for mice with induced subcutaneous RMA lymphoma, following subcutaneous administration of 50 µg of the substance of SEQ ID NO. 7, compared to control (PBS)
Figure 4:
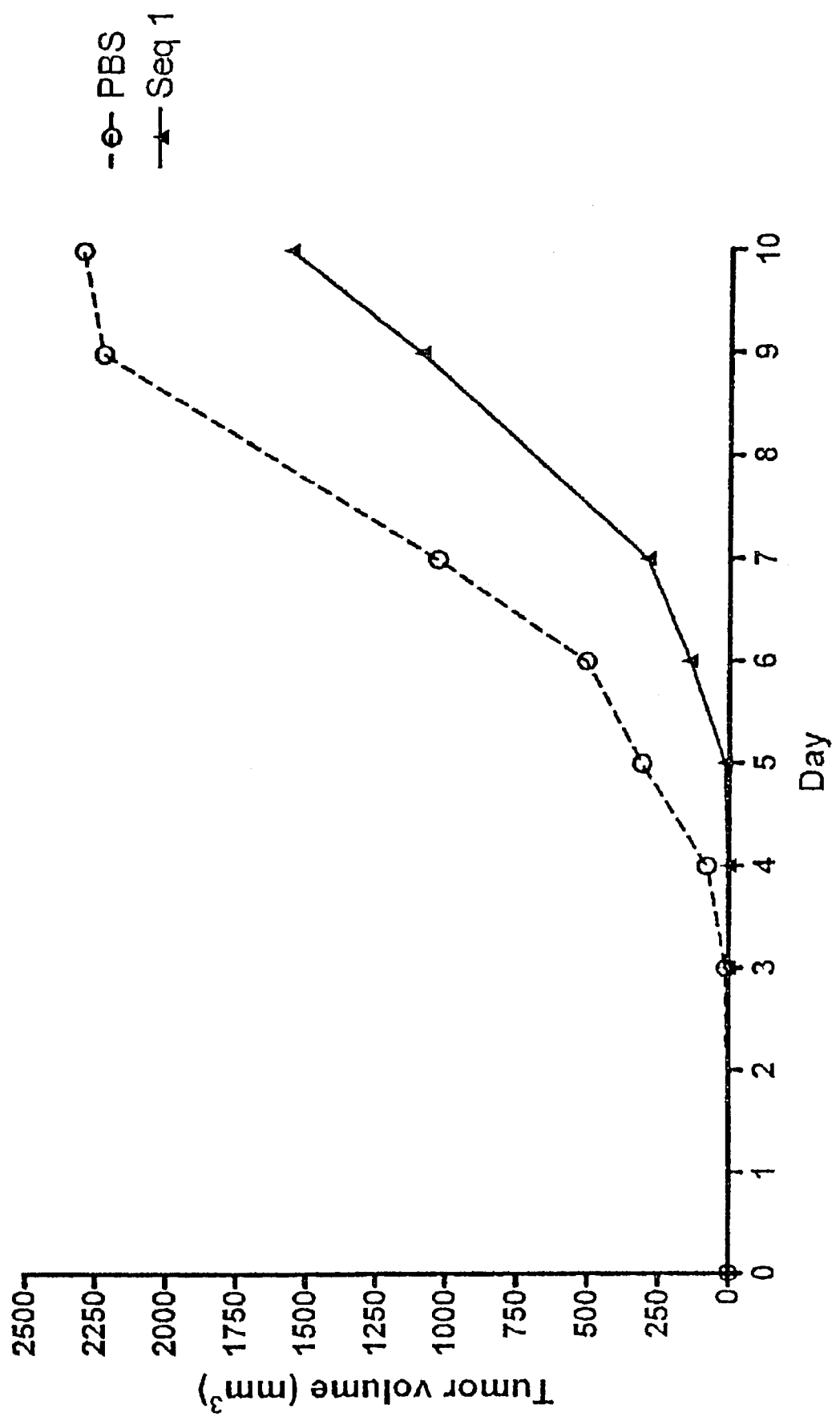
FIG. 4 is a graph showing tumour growth measured as tumour volume ($mm^3$) over time for mice with induced subcutaneous RMA lymphoma, following subcutaneous administration of 50 µg of the substance of SEQ ID NO. 1, compared to control (PBS)
Figure 5:
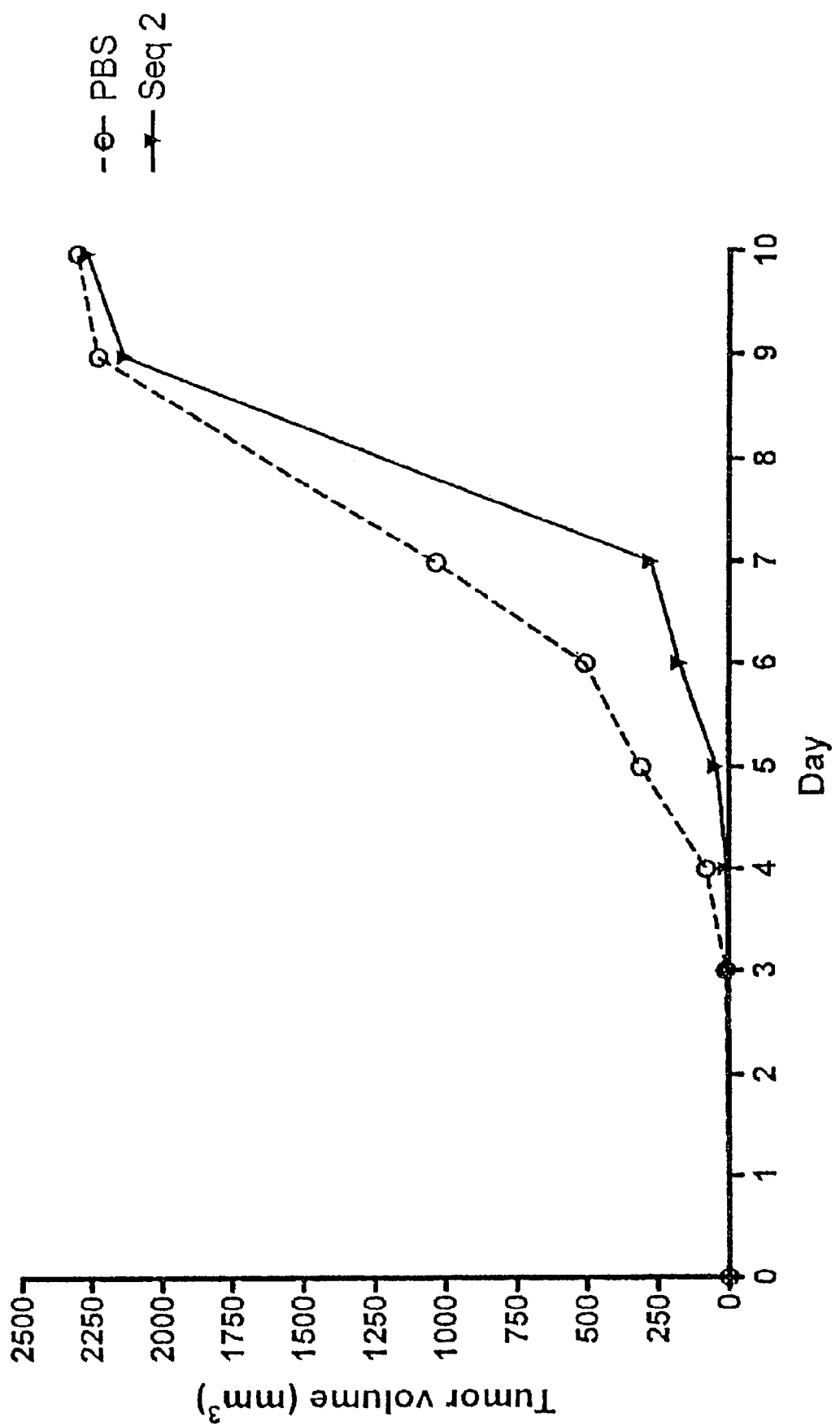
FIG. 5 is a graph showing tumour growth measured as tumour volume ($mm^3$) over time for mice with induced subcutaneous RMA lymphoma, following subcutaneous administration of 50 µg of the substance of SEQ ID NO. 2, compared to control (PBS)
Figure 6:
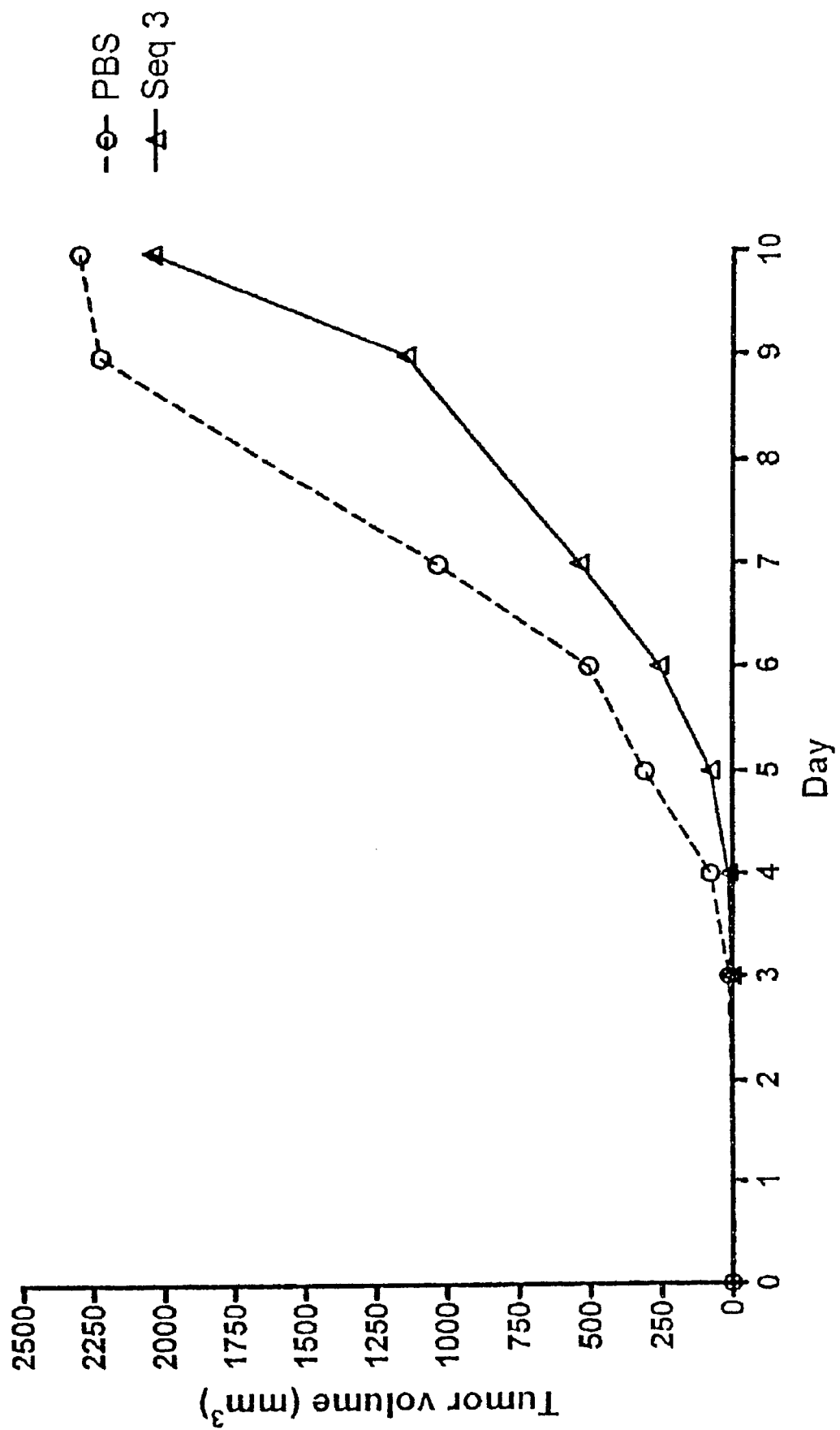
FIG. 6 is a graph showing tumour growth measured as tumour volume ($mm^3$) over time for mice with induced subcutaneous RMA lymphoma, following subcutaneous administration of 50 µg of the substance of SEQ ID NO. 3, compared to control (PBS)
Figure 7:
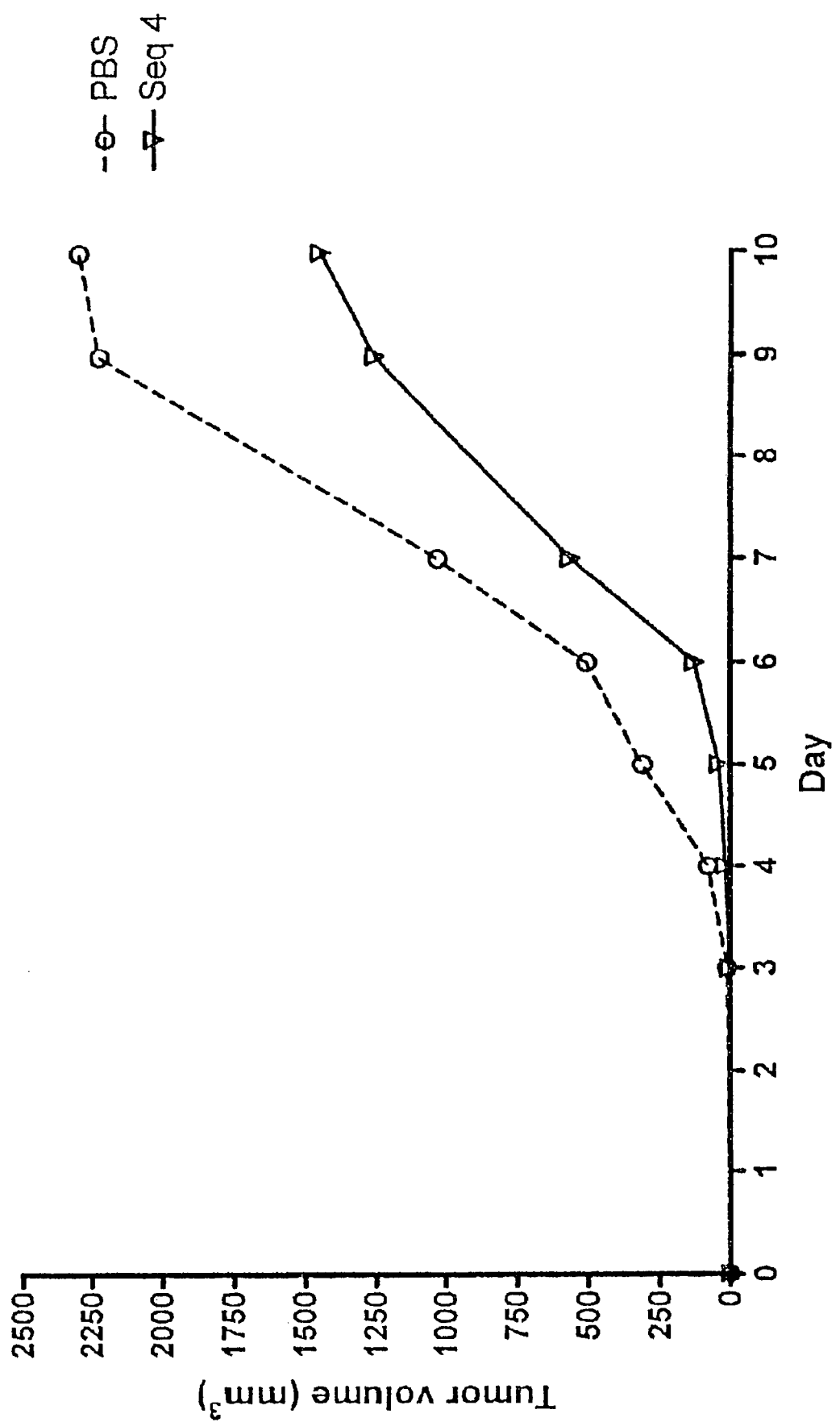
FIG. 7 is a graph showing tumour growth measured as tumour volume ($mm^3$) over time for mice with induced subcutaneous RMA lymphoma, following subcutaneous administration of 50 µg of the substance of SEQ ID NO. 4, compared to control (PBS)

Each tested compound showed an effect on tumour growth during the observation period of a maximum of 10 days. For SEQ ID NO 7 it was surprisingly seen that a lower dose (50 μg v. 150 μg) resulted in a pronounced reduction of tumour growth. Highly surprisingly, the same dose (50 μg) when administered nasally resulted in an equally large growth reduction (See FIGS. 1 and 2).

Among SEQ ID NO 1, 2, 3, 4 and 7 (FIG. 3-7) the effect was most pronounced for SEQ ID NO 1 and 7, at least in this experimental setting.

2. In Vitro Experiments with Human Cell Lines

Two recognized model cell lines for human cancer were used. The objective of the study was to investigate the capability of different oligonucleotides to inhibit tumour cell growth and to induce apoptosis in tumour cells. Another objective was to correlate the data obtained in animal studies with another set-up, predictive for the effect on cancer in humans. A positive control (a commercially available immunostimulatory oligonucleotide) was used, as well as a negative control (an artificial sequence containing a reversed CpG site).

2.1 Human Lymphoma Cell Line

The human Burkitt's lymphoma cell line Daudi was stimulated with each of the inventive nucleotides, SEQ ID NO 1-6 in tissue culture medium for 48 and 72 h. The expression of various surface expression markers was analyzed by FACS as described in literature (see e.g. GURSEL, et al. Differential and competitive activation of human immune cells by distinct classes of CpG oligodeoxynucleotide. J Leuk Biol. 2002, vol. 71, p. 813-820; JAHRSDORFER, et al. CpG DNA increases primary malignant B cell expression of costimulatory molecules and target antigens. J Leuk Biol. 2001, vol. 69, p. 81-88; JAHRSDORFER, et al. B-cell lymhomas differ in their responsiveness to CpG oligodeoxynucleotides. Clin Can Res. 2005, vol. 11, p. 1490-1499; and JAHRSDORFER, et al. Immunostimulatory oligodeoxynucleotides induce apoptosis of B cell chronic lymphocytic leukemia cells. J Leuk Biol. 2005, vol. 77, p. 378-387.) using the FACSarray instrument (BD Biosciences, San Jose, Calif., USA).

2.2 Human Colon Cancer Cell Line

The human colon cancer cell line HCT116 was stimulated with each of the inventive nucleotides, SEQ ID NO 1-5 and 7 in tissue culture medium for 72 h. The cell proliferation and cell death was analyzed by FACS analysis using Ki-67 and 7-amino actinomycin (7-AAD), respectively, staining according to procedures known to a skilled person. Ki-67 is expressed by proliferating cells, and using 7-AAD, apoptotic cells could be identified.

2.4 Results

Figure 8:
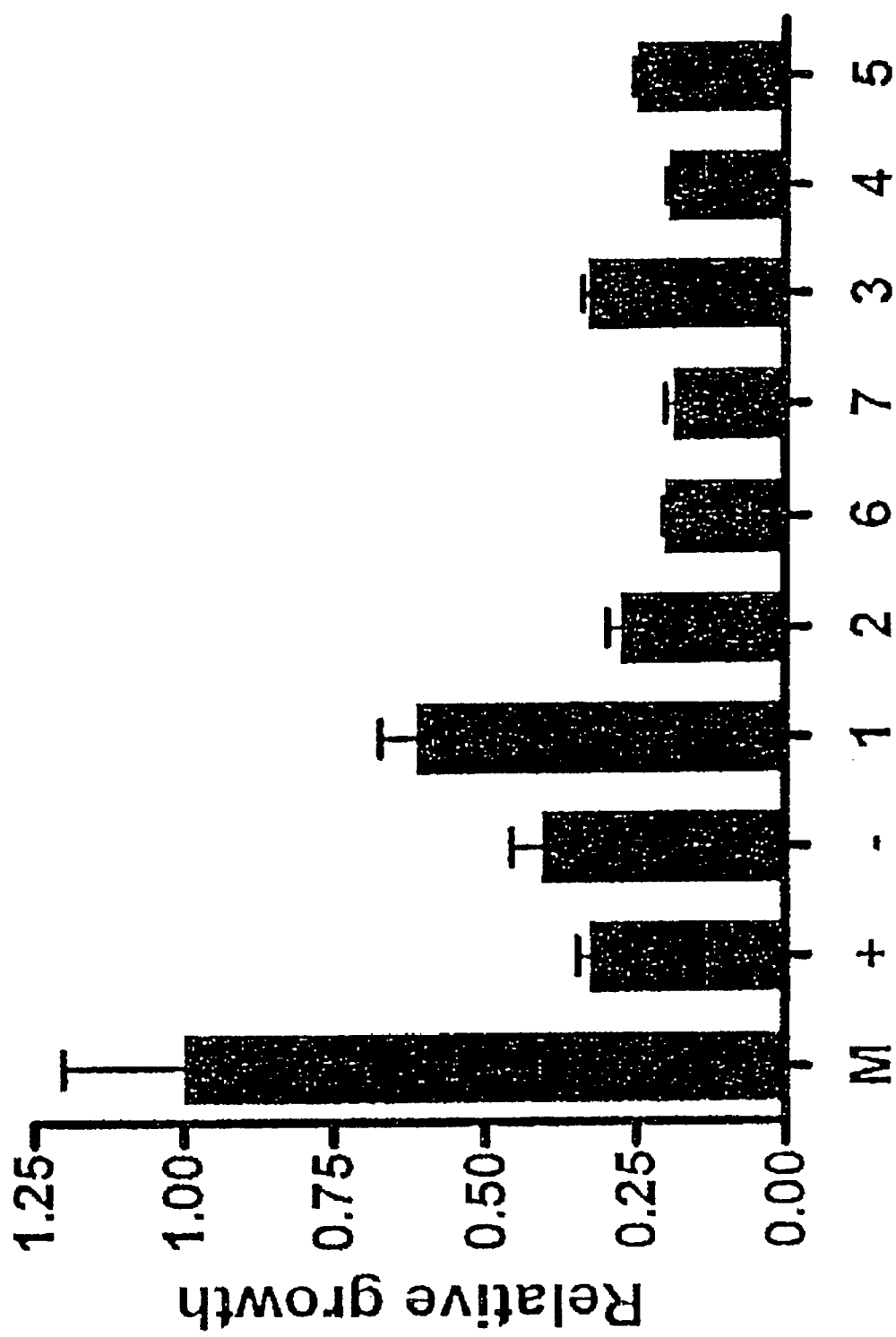
FIG. 8 is a bar diagram showing the growth reducing effect on a human colon cancer cell line HCT116 in vitro, following administration of the compounds according to SEQ ID NO. 1-7, wherein "+" and "−" denotes a positive and negative control, respectively.

As seen in FIG. 8, all compounds according to SEQ ID NO 1-7 are capable of reducing tumour growth to some extent. However did in particular SEQ ID NO 2-5 and 7 achieve marked reduction of tumour growth compared to the untreated cells (positive control).

Figure 9:
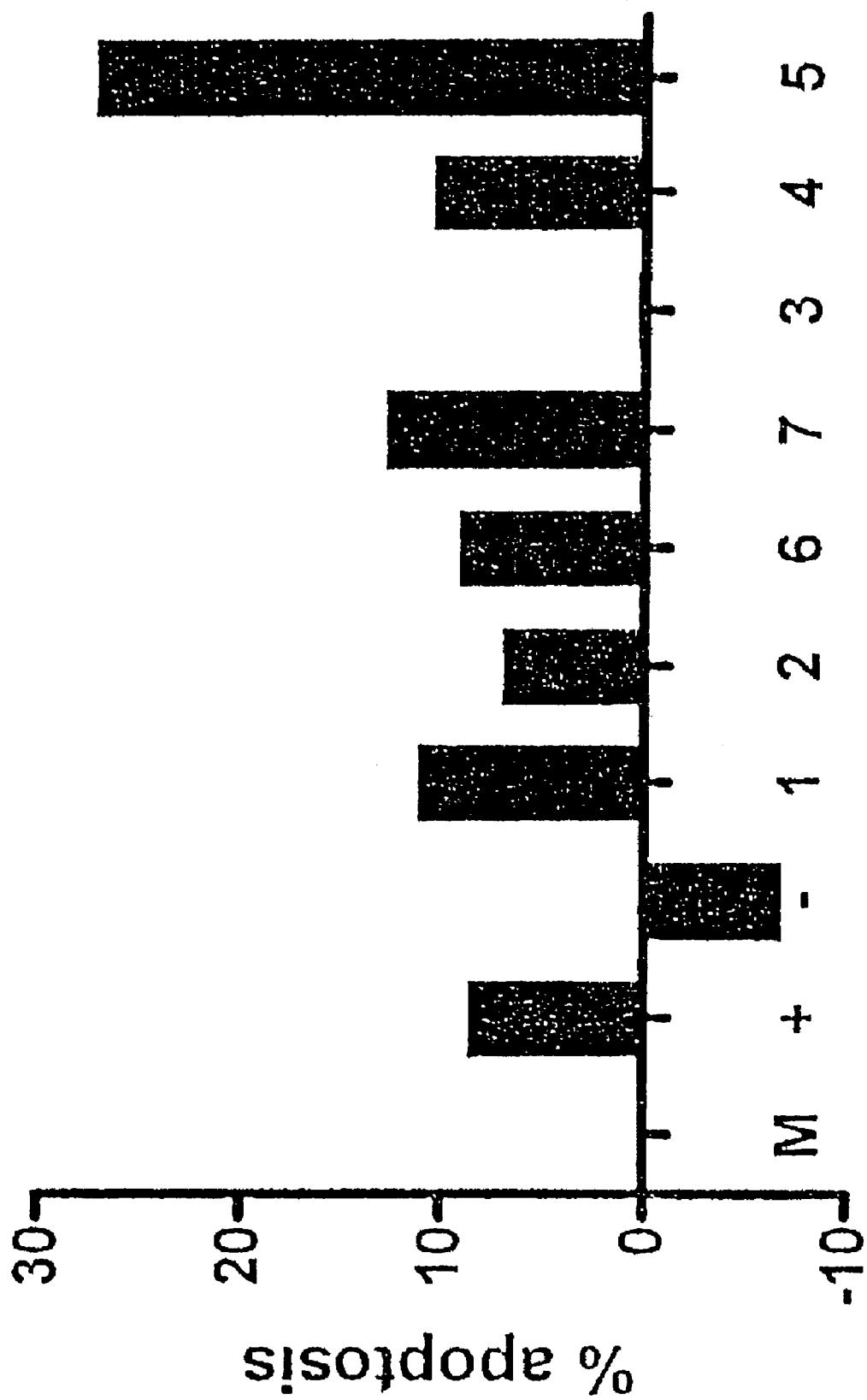
FIG. 9 is a bar diagram showing apoptosis induction in a human colon cancer cell line HCT116 in vitro, following administration of the compounds according to SEQ ID NO. 1-7, wherein "+" and "−" denotes a positive and negative control, respectively.

FIG. 9 shows the capability of the same compounds to induce apoptosis, and here the compounds, in particular SEQ ID NO 1, 5 and 7 induced a high rate of apoptosis compared to the untreated cells.

As shown in FIG. 10, all sequences, except SEQ ID NO 7 stimulated the expression of the B-cell proliferation markers CD20, CD40 and CD54.

Figure 11A:
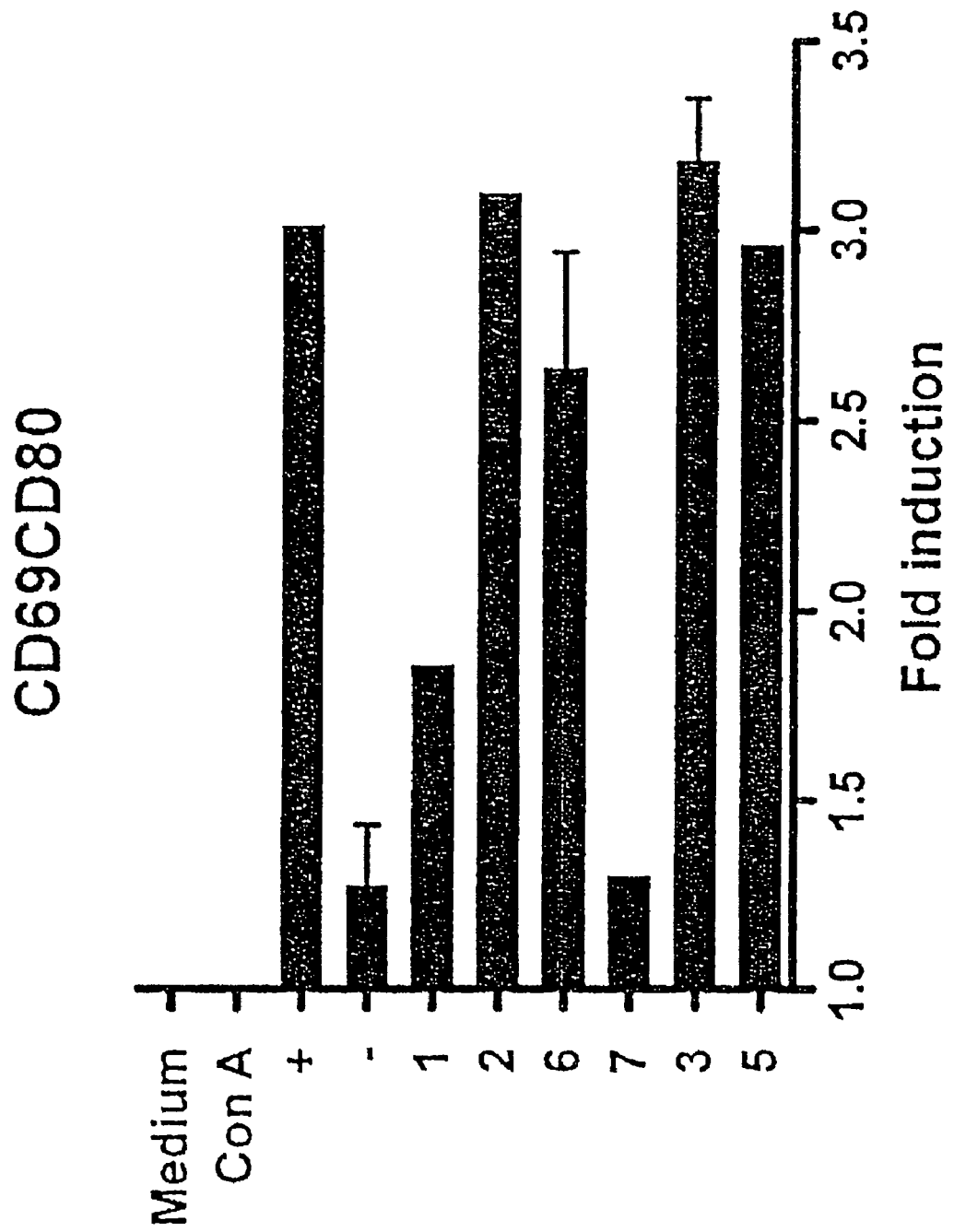
FIG. 11 consists of two bar diagrams (11 a and b) showing the effect on the expression of the B-cell activation markers CD69, CD80, and CD86 respectively in a human B-cell lymphoma model in vitro, following administration of the compounds according to SEQ ID NO. 1-7.
Figure 11B:
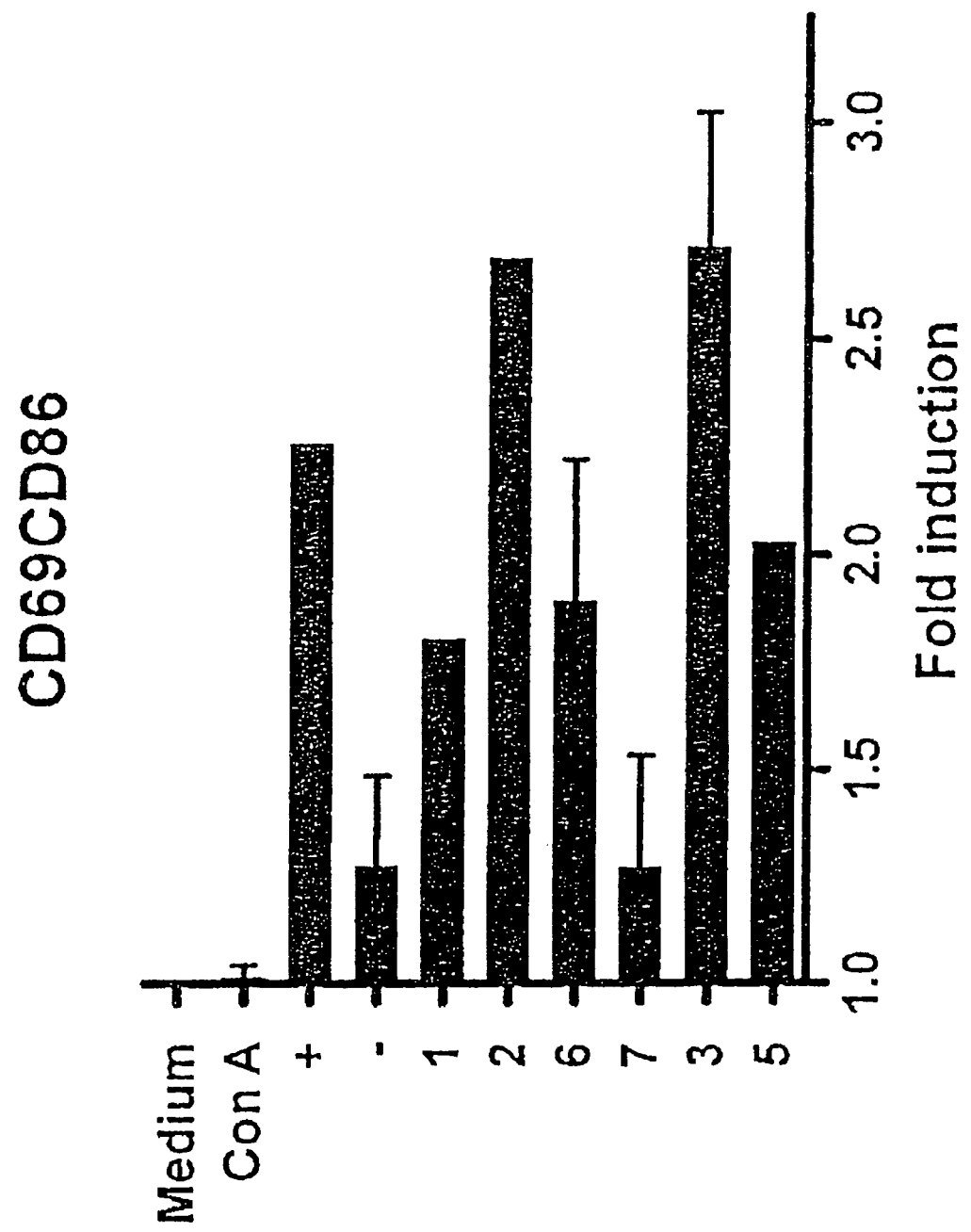

FIG. 11 on the other hand shows the up-regulation of the B-cell activation markers CD69, CD80 and CD86 following treatment with all sequences, with SEQ ID NO 7 being the weakest inducer of B-cell activation.

Figure 12:
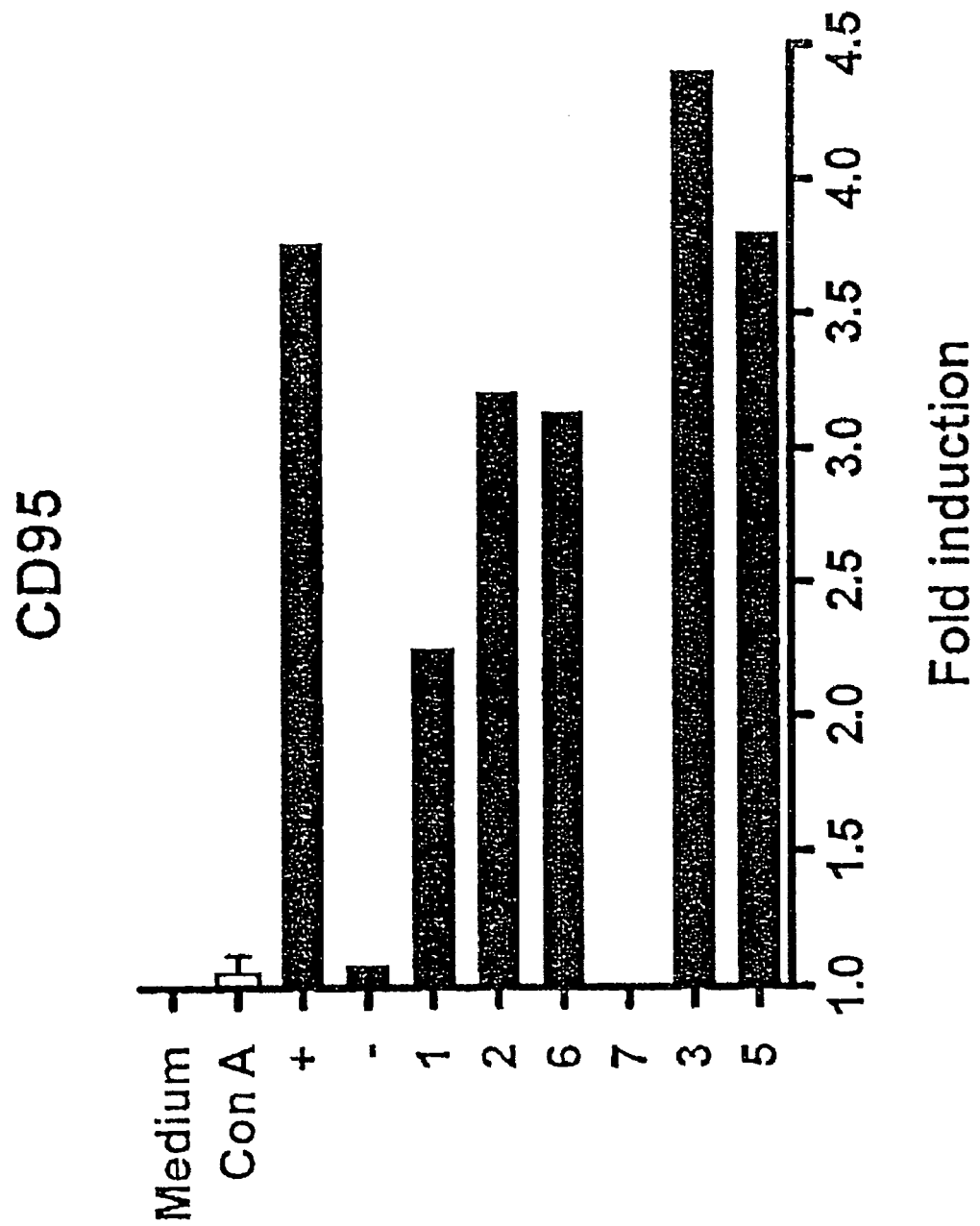
FIG. 12 is a bar diagram showing the effect on the expression of the apoptosis marker CD95 in a human B-cell lymphoma model in vitro, following administration of the compounds according to SEQ ID NO. 1-7.

FIG. 12 shows that treatment with all the sequences, except SEQ ID No 7, resulted in a marked increase of the apoptotic receptor CD95 (also know as the FAS receptor).

Experiments Performed During the Priority Year

3. Receptor Expression in PBMCS Isolated from Healthy Subjects 3.1 Materials and Methods Heparinized peripheral blood was obtained from healthy subjects (n=3).

The mononuclear cell fraction was isolated by Ficoll-Hypaque (Seromed, Berlin, Germany) gradient centrifugation. The cells were immediately incubated at 37° C. in a volume of 500 μl of complete RPMI-medium (containing 10% FCS, 1% PenStrep, 2 mM L-glutamine, 10 mM HEPES and 1 mM Sodium Pyruvate) in 48-well plates at a conc. of 2×10$^6$ cells/ ml and treated with 1, 10 and 25 μM of each of 10 different oligonucleotide compounds. A fraction of the cells were stained with two mixes of 4 antibodies each (CD19, CD20, CD23, CD80 and CD3, CD25, CD56 CD69) for direct analysis of surface antigen expression by FACS.

After 48 hours, 200 μl of the cells were spun down in 96-well plates, resuspended in 100 μl of 2% FCS (in PBS) and incubated with two sets of antibody mixes (as above) for 30 min at 4° C. The cells were then washed twice in pure PBS and subsequently analyzed by FACS using a FACSArray bioanalyzer for surface antigen expression analysis. After 4 days from day 0, the remainder of the cells was harvested for apoptosis analysis. The cells were spun down in 96-well plates, resuspended in 2% FCS as above and incubated with an antibody mix of CD19 and CD3 (BD Pharmingen) for 30 min at 4° C. The cells were washed twice with PBS and subsequently stained with Annexin V and 7-AAD for 10 min at RT for analysis of early and late apoptosis, respectively. The cells were analyzed by flow cytometry as above.

3.2 Results

Figure 23:
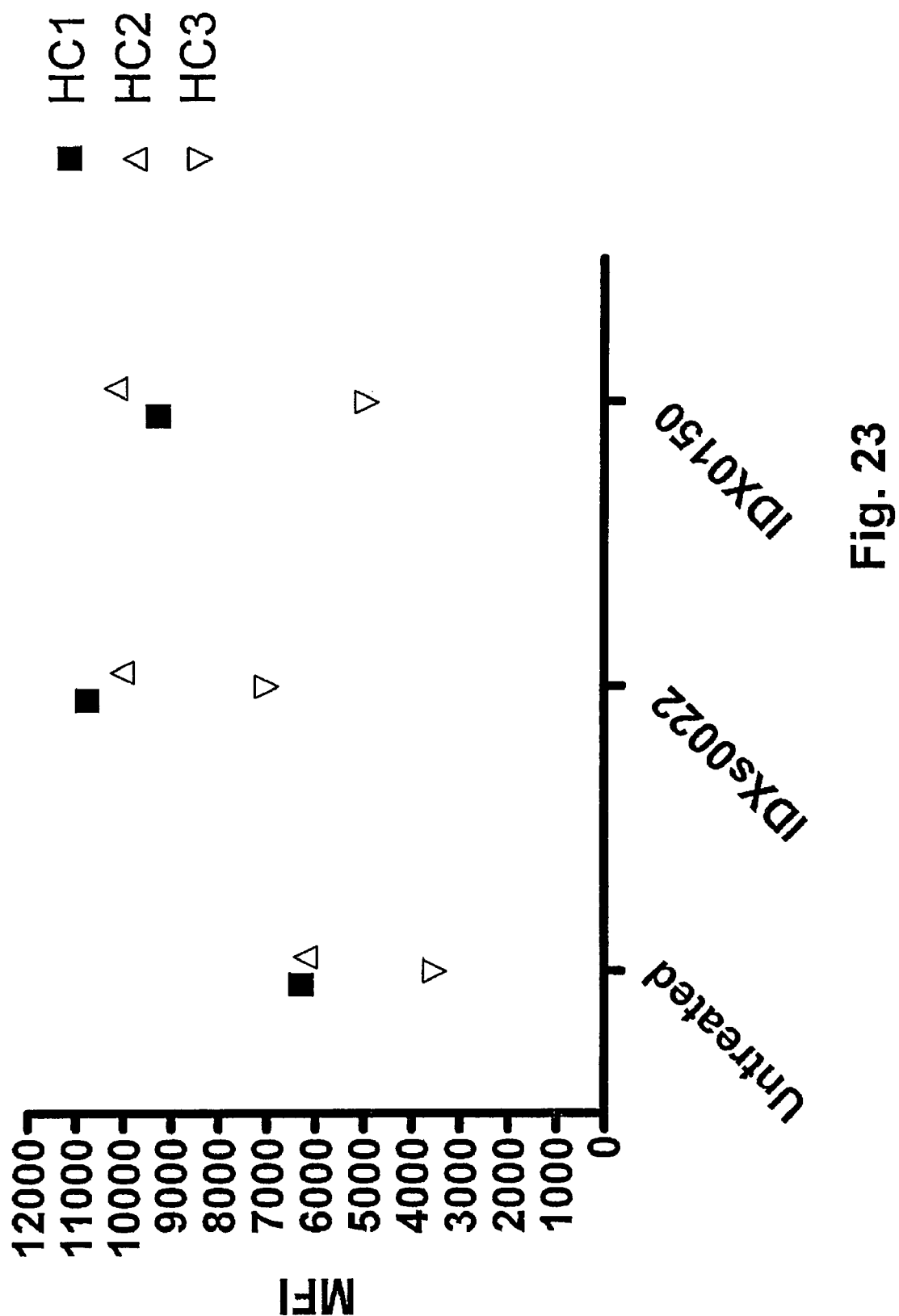
FIG. 23 shows the expression of CD20 measured in PBMCs from three healthy controls, achieved by the administration of SEQ ID NO 3 at 10 µM.
Figure 24:
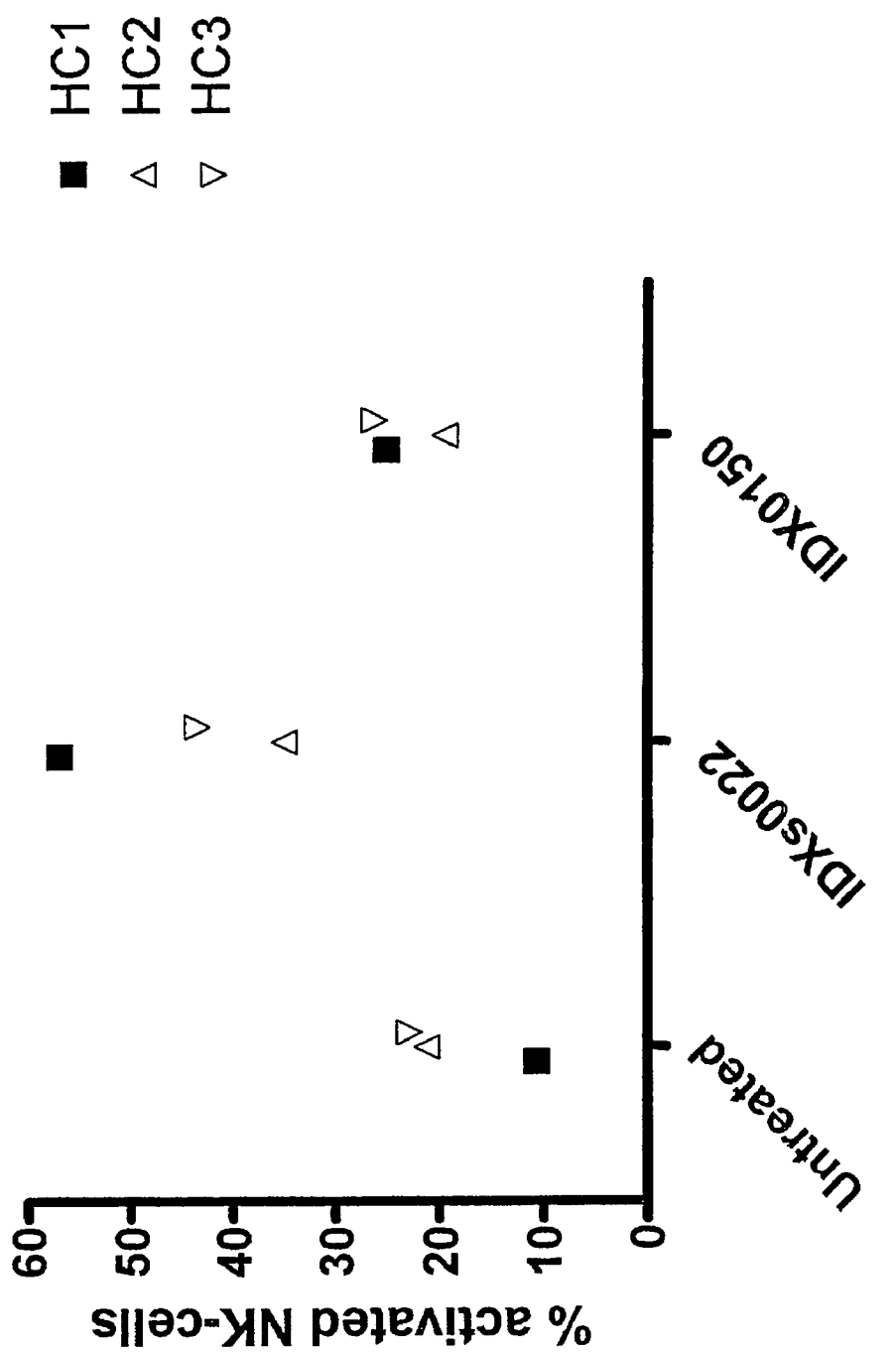
FIG. 24 shows the induction of NK-cell activation (CD69) achieved by SEQ ID NO 3 at 10 µM, as compared to untreated and positive control, SEQ ID NO 6.

The results indicate that the expression of CD20 and CD23 was up-regulated by the administration of SEQ ID NO 3 at 10 µM (FIG. 23 and data not shown) and that induction of NK-cell activation (CD69) was achieved by SEQ ID NO 3 at 10 µM, as compared to untreated and positive control, SEQ ID NO 6 (FIG. 24). After 4 d incubation with oligonucleotide compounds, the apoptosis of T- and B-cells was not altered (data not shown).

4. Receptor Expression in PBMCs Isolated from CLL and FL Patients 4.1 Materials and Methods Heparinized peripheral blood was obtained after informed consent from patients (n=5) with B-chronic lymphocytic leukemia (B-CLL) and follicular lymphoma (FL) with significant circulating disease. All patients were diagnosed by routine immunophenotypic, morphologic and clinical criteria.

The mononuclear cell fraction was isolated by Ficoll-Hypaque (Seromed, Berlin, Germany) gradient centrifugation. The cells were immediately incubated at 37° C. in a volume of 500 µl of complete RPMI-medium (containing 10% FCS, 1% PenStrep, 2 mM L-glutamine, 10 mM HEPES and 1 mM Sodium Pyruvate) in 48-well plates at a conc. of $2 \times 10^6$ cells/ml and treated with 1, 10 and 25 µM of each of 10 different oligonulecleotide compounds. A fraction of the cells were stained with two mixes of 4 antibodies each (CD19, CD20, CD23, CD80 and CD3, CD25, CD56 CD69) for direct analysis of surface antigen expression by FACS.

After 48 hours, 200 µl of the cells were spun down in 96-well plates, resuspended in 100 µl of 2% FCS (in PBS) and incubated with two sets of antibody mixes (as above) for 30 min at 4° C. The cells were then washed twice in pure PBS and subsequently analyzed by FACS using a FACSArray bioanalyzer for surface antigen expression analysis. After 4 days from day 0, the remainder of the cells was harvested for apoptosis analysis. The cells were spun down in 96-well plates, resuspended in 2% FCS as above and incubated with an antibody mix of CD19 and CD3 (BD Pharmingen) for 30 min at 4° C. The cells were washed twice with PBS and subsequently stained with Annexin V and 7-AAD for 10 min at RT for analysis of early and late apoptosis, respectively. The cells were analyzed by flow cytometry as above.

4.2 Results

Figure 13:
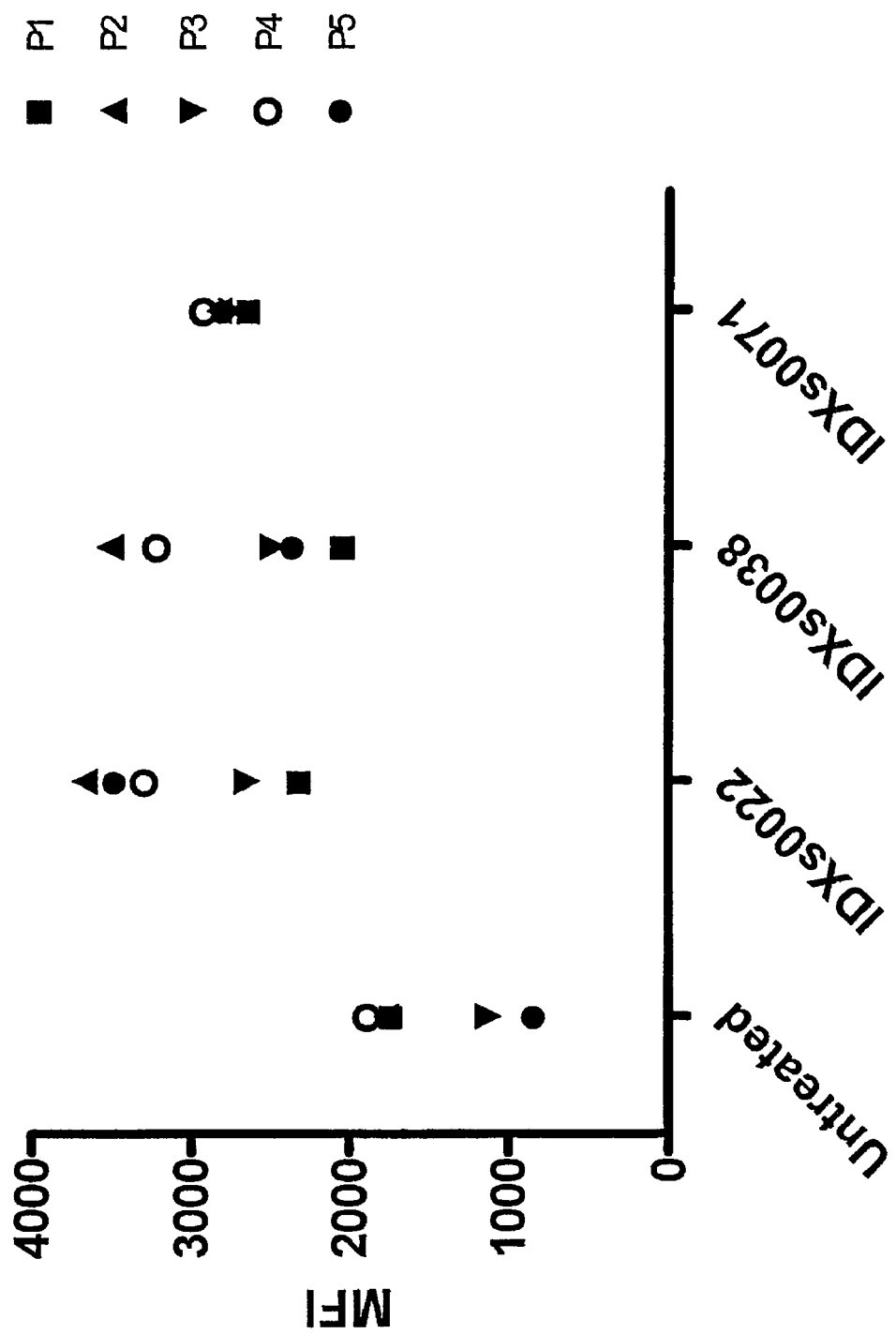
FIG. 13 is a graph showing how the experimental compounds induce up-regulation of CD20n on B-cells from CLL-patients. At the tested concentration, 10 µM, the compounds IDXs0022, 0038 and 0071 all show a significant effect. These compounds correspond to SEQ ID NO 3, 8, and 9 in Table 1.
Figure 14:
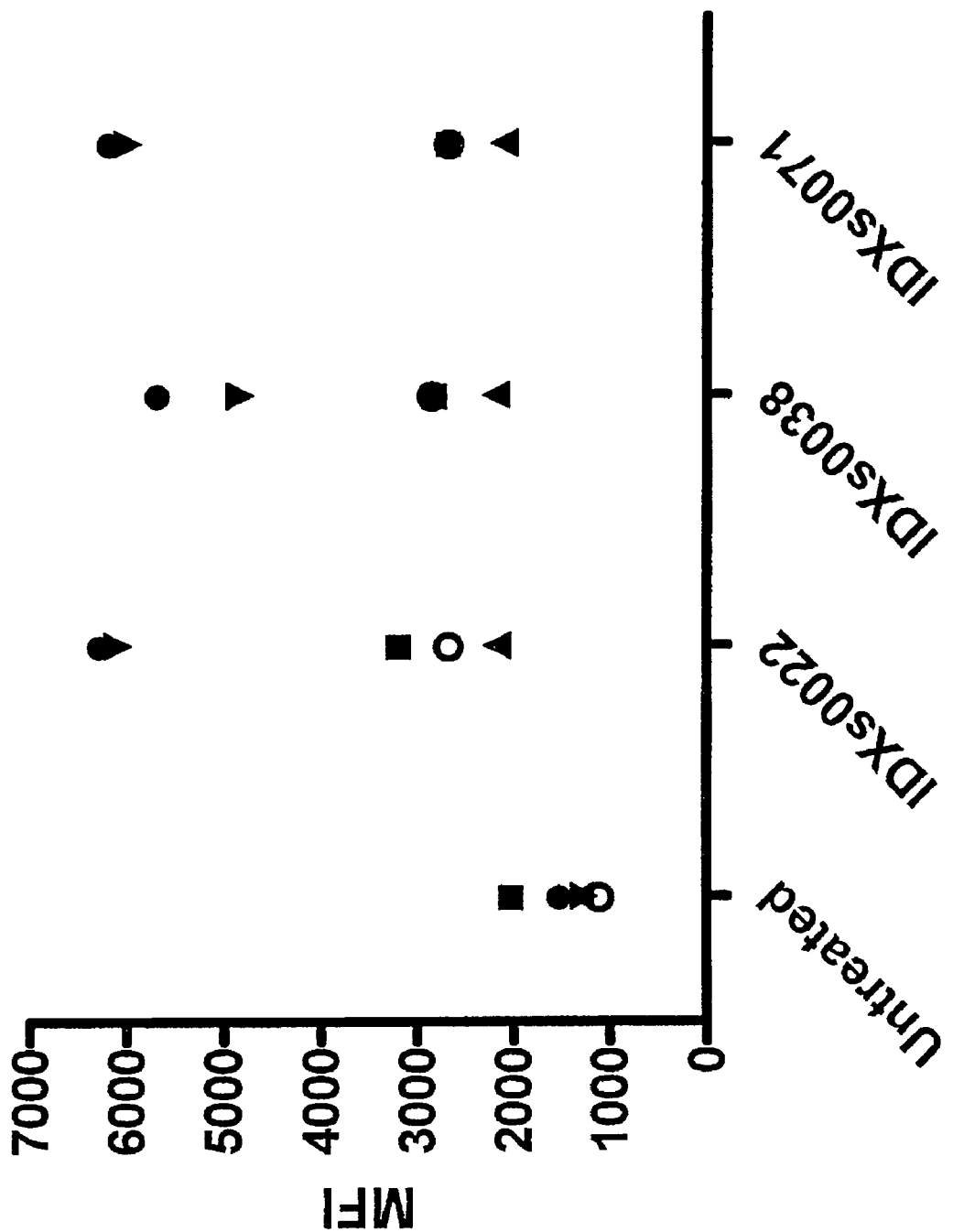
FIG. 14 similarly shows the up-regulation of CD80 on B-cells from CLL-patients. Also here, the compounds represented by SEQ ID NO 3, 8, and 9 show effect compared to the untreated control.

The results show that SEQ ID NOs 3, 8, and 9 induce up-regulation of CD20 on B-cells from CLL-patients (FIG. 13), as well as the up-regulation of CD80 on B-cells from CLL-patients (FIG. 14). The expression of CD23 and CD25 was also up-regulated (data not shown).

Figure 15:
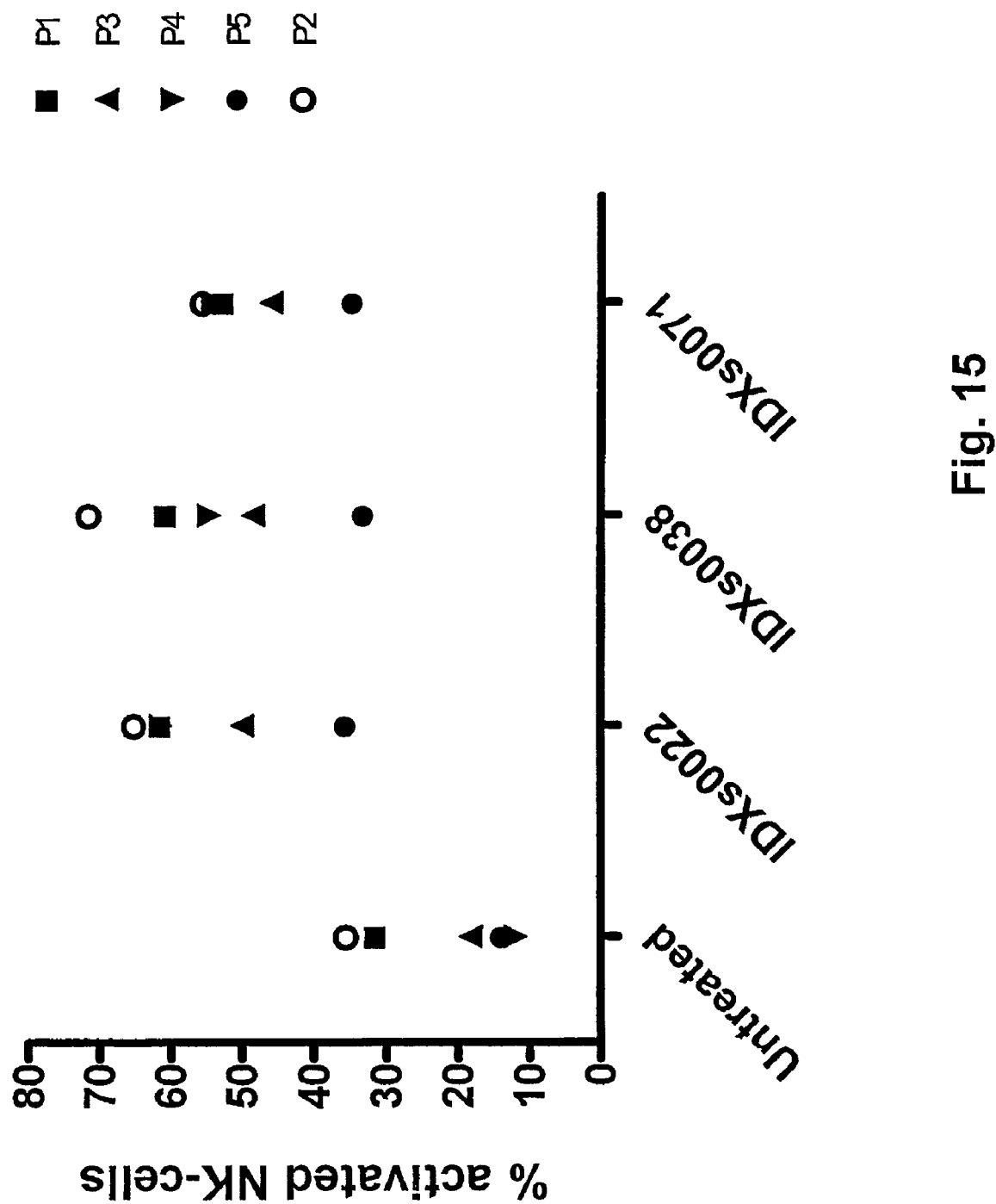
FIG. 15 shows how the experimental compounds induce activation of NK-cells in PBMC from CLL-patients. Again, the compounds represented by SEQ ID NO 3, 8, and 9 show effect compared to the untreated control.

It was also shown that SEQ ID NOs 3, 8 and 9 induce activation of NK-cells as measured by CD69 staining (FIG. 15).

Figure 16:
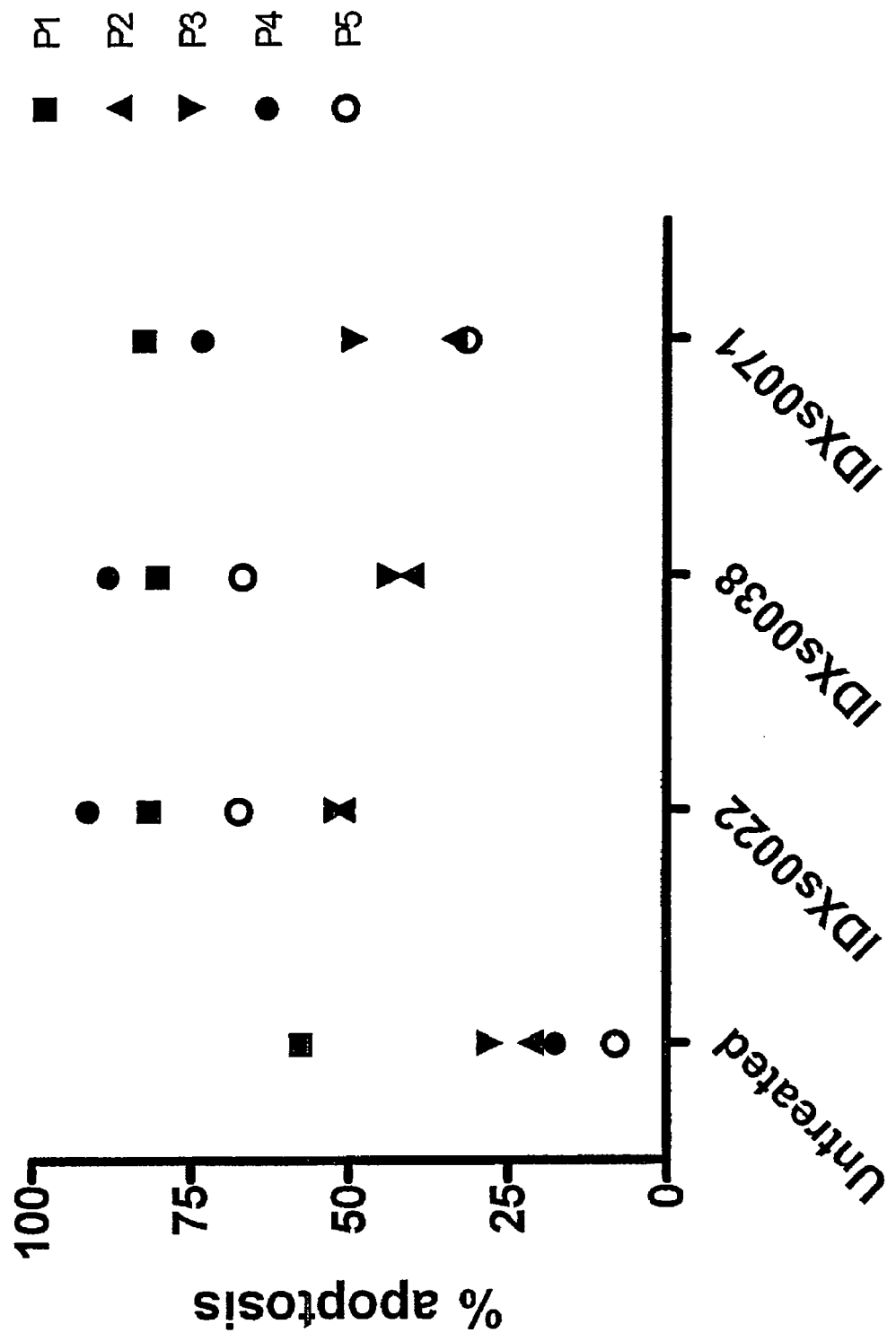
FIG. 16 shows that the experimental compounds induce apoptosis of T-cells in PBMCs from CLL-patients. The tested compounds show effect, and compound IDXs0022, corresponding to SEQ ID NO 3 is most potent at the tested concentration, 10 µM.
Figure 17:
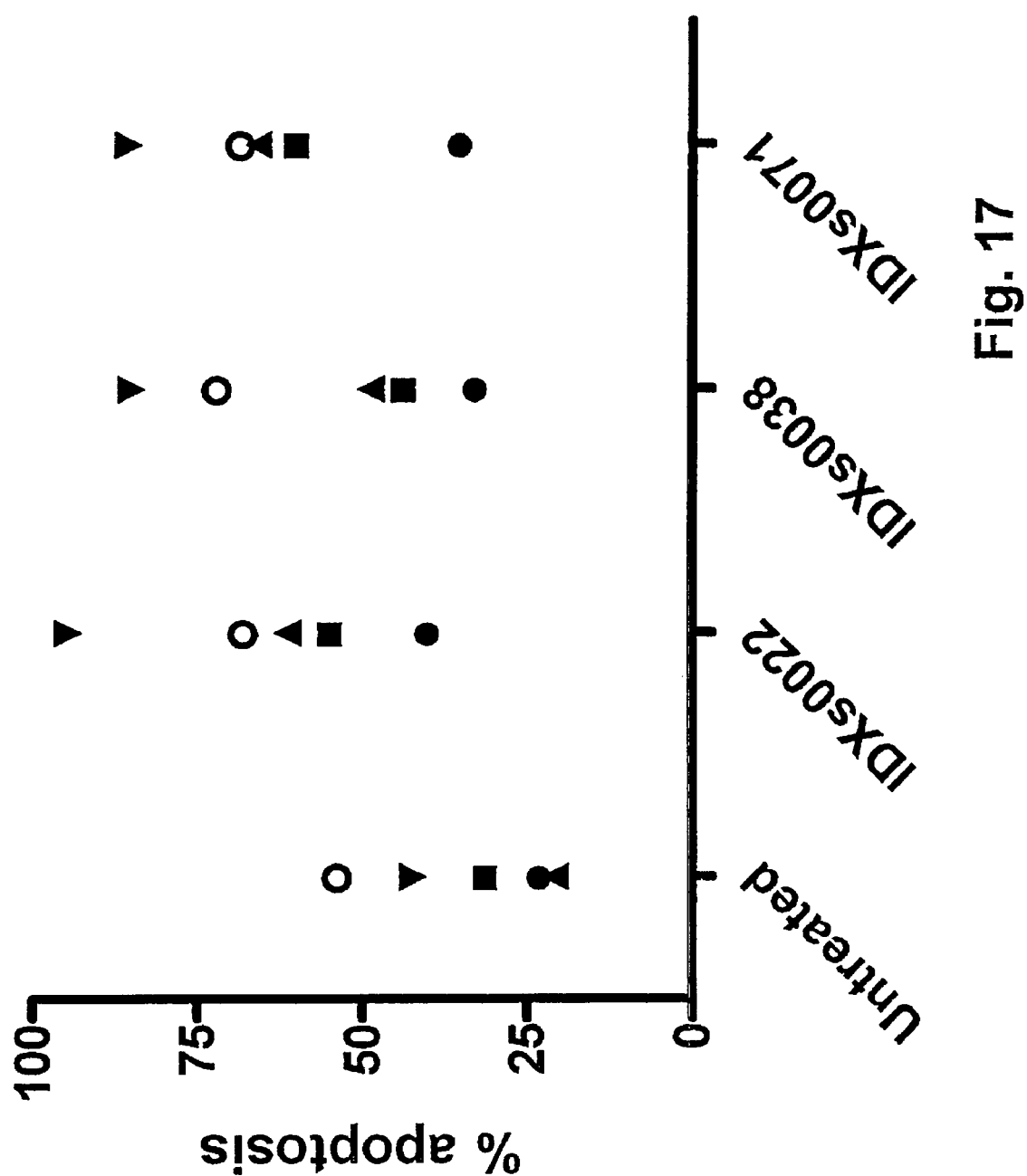
FIG. 17 shows that the experimental compounds induce apoptosis also of B-cells in PBMCs from CLL-patients. All tested compounds show effect, and compound IDXs0022, corresponding to SEQ ID NO 3 is again most potent at the tested concentration, 10 µM.

The results also indicate that SEQ ID NOs 3, 8 and 9 induce apoptosis of T-cells and B-cells in PBMCs from CLL-patients (FIGS. 16 and 17).

5. Pulse Experiment 5.1 Experimental Setup

The cytokine profile and expression of surface markers was determined in a so called pulse experiment using PBMCs from a healthy control. The cytokine profile was determined after 48 h cultivation in vitro and the surface marker staining (FACS) performed after 72 h.

The PBMCs were prepared and cultivated as described in Examples 3 and 4. The PBMCs were then subjected to the experimental compounds for a predetermined period, followed by washing. The washing was performed as follows: First the plates were centrifuged at 1500 rpm for 5 min. Then supernatant was discarded and new medium added. The centrifugation was repeated, and the second supernatant discarded and fresh medium added. After that, the PBMCs were cultivated further until the desired time points 48 h (cytokine profile), or 72 h (surface marker staining).

The cytokine profile was determined after 48 h in vitro cultivation. In the first batch, the PBMCs were only cultivated 48 h without having been subjected to the experimental compound. In a second batch, the PBMCs were subjected to a 30 min pulse with SEQ ID NO 3 (IDXs0022), or in other words, exposed to SEQ ID NO 3 for 30 min, washed as described above, and then cultivated for 48 h. In a third batch, the PBMCs were subjected to a 2 h pulse, and in a fourth batch, subjected to SEQ ID NO 3 for 6 h. The following cytokines were analysed: Il-6, Il-10, and IP-10. The cytokine concentration is given as pg/ml.

The surface marker staining was performed 72 h after in vitro cultivation. In the first batch, the PBMCs were only cultivated 72 h without having been subjected to the experimental compound. In a second batch, the PBMCs were subjected to a 30 min pulse with SEQ ID NO 3 (IDXs0022), or in other words, exposed to SEQ ID NO 3 for 30 min, washed as described above, and then cultivated for 72 h. In a third batch, the PBMCs were subjected to a 2 h pulse, and in a fourth batch, subjected to SEQ ID NO 3 for 6 h. The surface marker analysis was performed by direct analysis of surface antigen expression of CD19, CD20, CD56 and CD69 by FACS 3.2. Results The results show that there is a pronounced long term effect also where the oligonucleotide has been removed by washing after only 30 min, which supports the feasibility of nasal administration, or administration to other mucous membranes where the oligonucleotide is not expected to reside for more than about 30 min.

Figure 18:
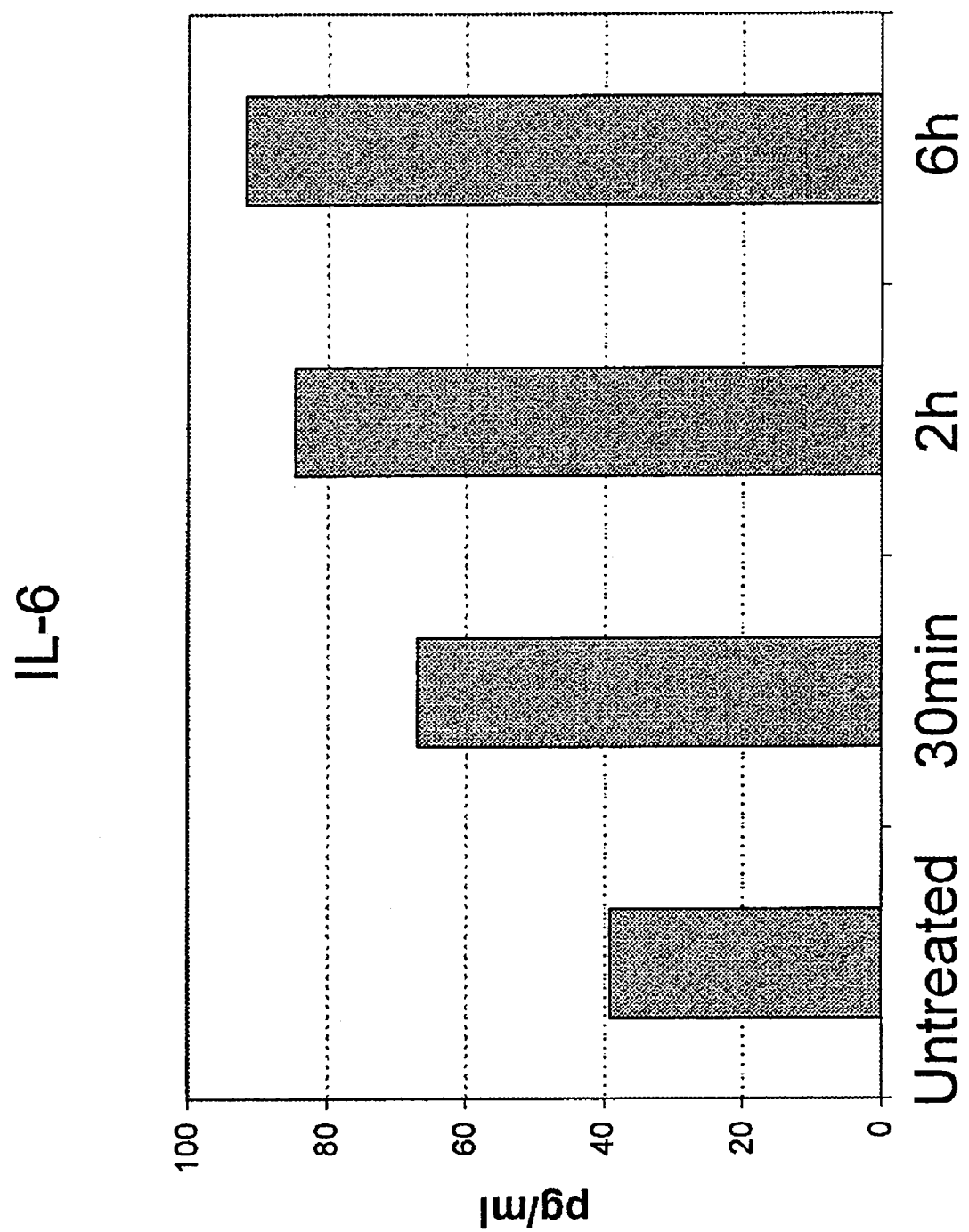
FIG. 18 shows the up-regulation of the cytokine IL-6 in PBMCs from a healthy control for SEQ ID NO 3 at the concentration of 25 µM, and following 30 min, 2 h and 6 h exposure, compared to untreated.
Figure 19:
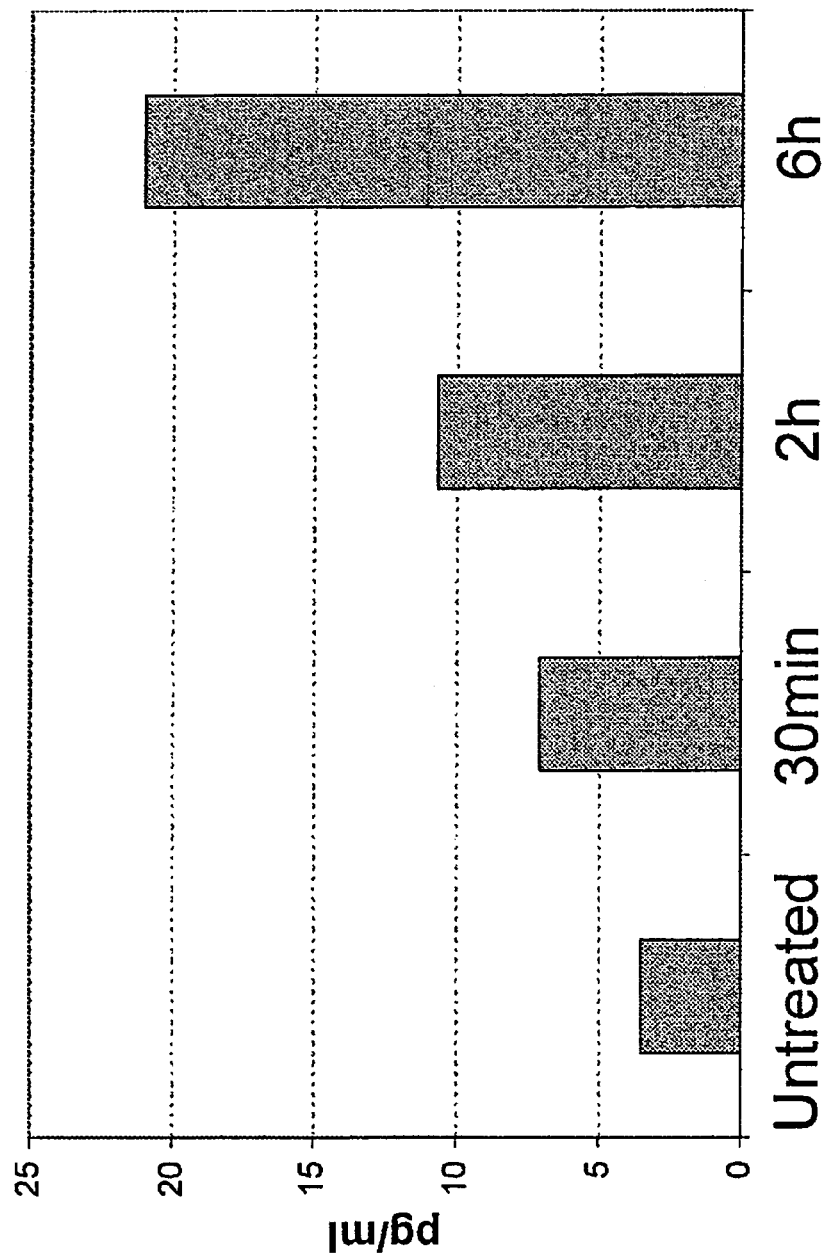
FIG. 19 shows the up-regulation of the cytokine IL-10 in PBMCs from a healthy control for SEQ ID NO 3 at the concentration of 25 µM, and following 30 min, 2 h and 6 h exposure, compared to untreated.
Figure 20:
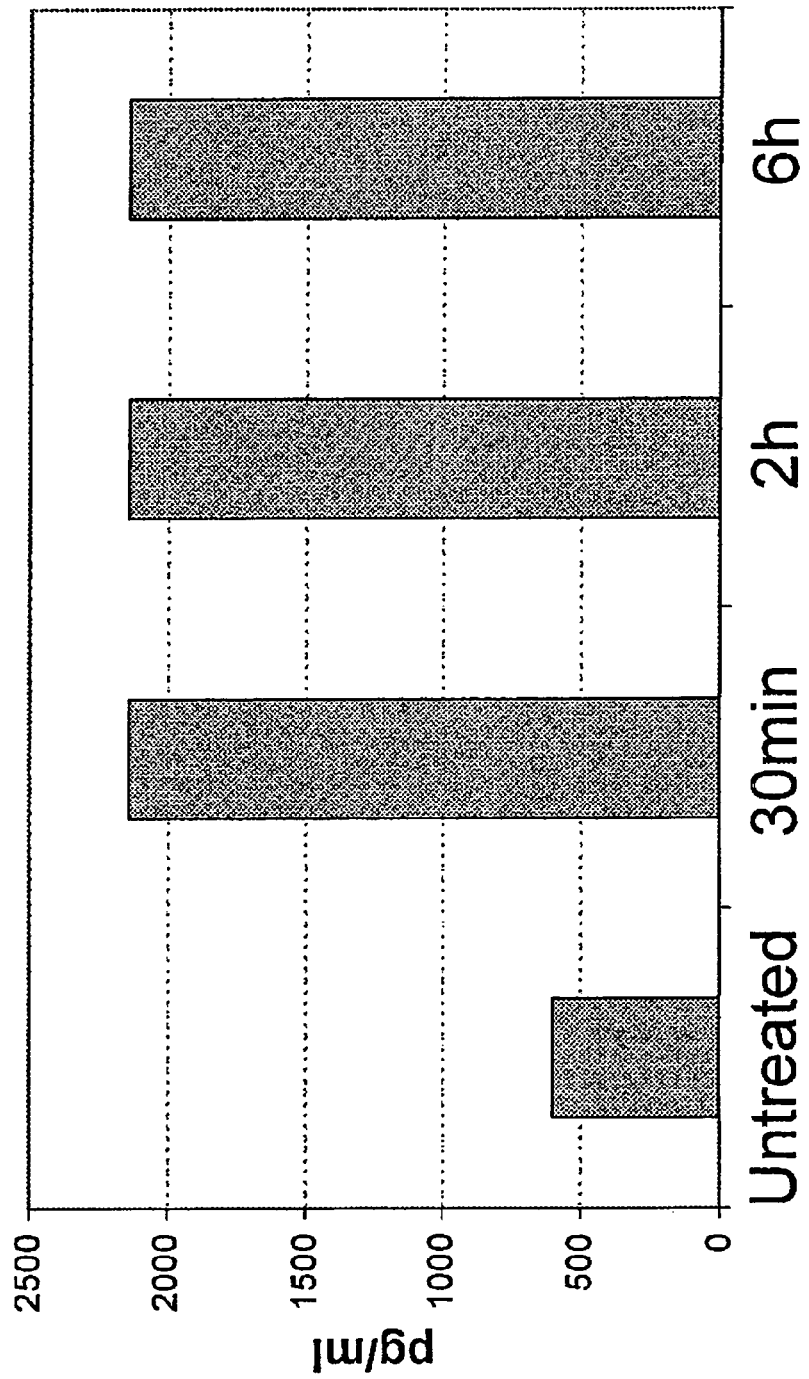
FIG. 20 shows the up-regulation of the cytokine IP-10 in PBMCs from a healthy control for SEQ ID NO 3 at the concentration of 25 µM, and following 30 min, 2 h and 6 h exposure, compared to untreated.
Figure 21:
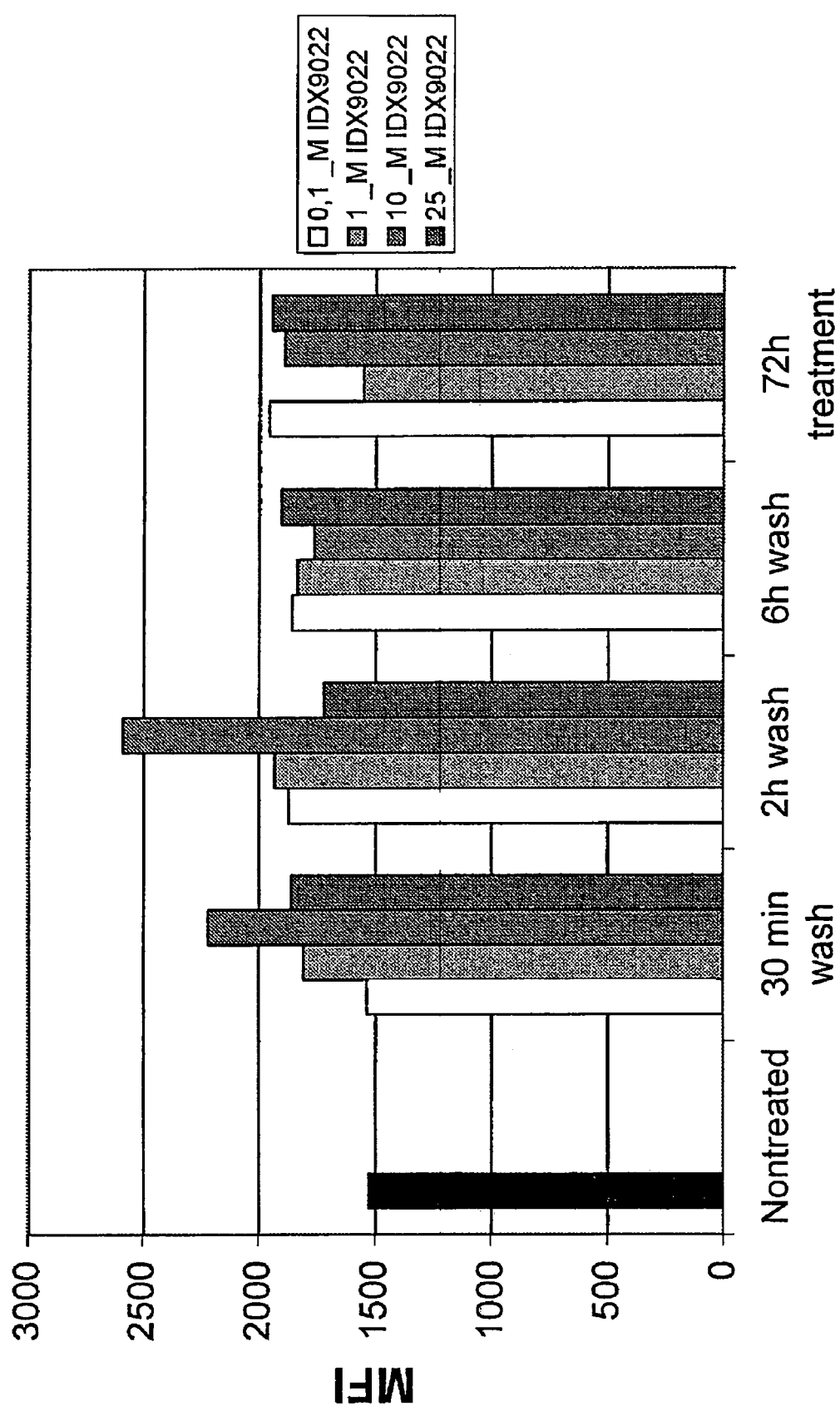
FIG. 21 shows the up-regulation of CD20 expression in PBMCs from healthy controls for SEQ ID NO 3 at the concentrations 0.1, 1, 10 and 25 µM, and following 30 min, 2 h and 6 h exposure, compared to untreated and 72 h exposure.
Figure 22:
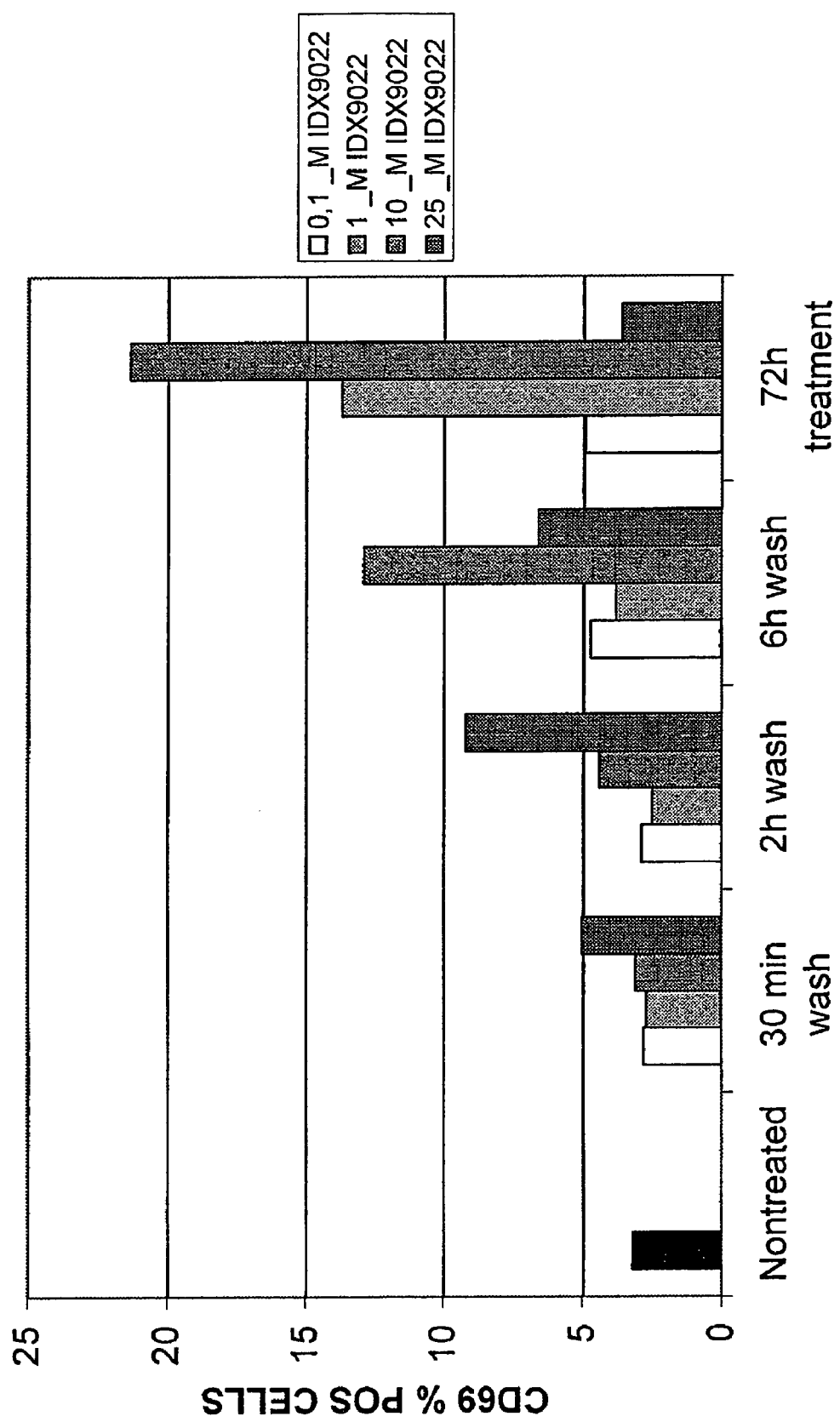
FIG. 22 shows the activation of NK-cells in PBMCs from healthy controls at different concentrations, and following 30 min, 2 h and 6 h exposure, compared to untreated and 72 h exposure, using SEQ ID NO 3.

The results also show a pronounced effect when the oligonucleotide was removed by washing after 2 h and even after 6 h, corresponding e.g. to rectal administration, where a longer residence time is expected. The results are shown in FIGS. 18, 19, and 20 for the cytokine analysis and FIGS. 21 and 22 for the surface marker staining.

It should also be noted that this experiment was performed using human PBMCs which makes the results transferable to an in vivo setting with better accuracy than experiments performed with immortalized human cell lines, another usual experimental setting. Notably PBMCs obtained from a diseased patient will contain e.g. the B-cells and the effect of the experimental compounds is seen directly on the relevant targets for the therapy.

REFERENCES

U.S. Pat. No. 6,498,147 B (THE SCRIPPS INSTITUTE) Dec. 24, 2002

KRIEG, A M. Lymphocyte activation by CpG dinucleotide motifs in prokaryotic DNA. Trends Microbiol. 1996, vol. 4, no. 2, p. 73-6.

KRIEG, A M, et al. Mechanisms and therapeutic applications of immune stimulatory cpG DNA. Pharmacol Ther. 1999, vol. 84, no. 2, p. 113-20.

WOOLDRIDGE, J E, et al. CpG DNA and cancer immunotherapy: orchestrating the antitumour immune response. Curr Opin Oncol. 2003 November, vol. 15, no. 6, p. 440-5.

CALIGARIS-CAPPIO, F., Hamblin, T. J.: Ball chronic lymphocytic leukemia: a bird of a different feather. J Olin Oncol. 1999 17:399406.

ROZMAN, C., Montserrat, E.: Chronic lymphocytic leukemia. New Engl J. Med. 1995 333: 1052-1059.

GAIDAN, G. L., Ballerini, P., Gong J Z, et al: p53 mutations in human lymphoid malignancies: association with Burkitt lymphoma and chronic lymphocytic leukemia. Proc Nat Acad Sci USA. 1991 88:54I 3-541 8.

DOHNER, H., Stilgenbauer, S., Doner, K., Bentz, M., Lichter, P.: Chromosome aberration in B-cell chronic lymphocytic leukemia: reassessment based on molecular genetic analysis. J Mol Med. 1999 77:266-270.

OSORIO, L. M., Jondal, M. Aguilar-Santelises, M.; Regulation of BOLL Apoptosis Through Membrane Receptors and Bcl-2 Family Proteins; Leukemia and Lymphoma. 1999 30:247-256.

DANCESCU, M., Rubio-Trujillo M, Biron G, Bron D, Delespesse G, Sarfati M. Interleukin 4 protects chronic lymphocytic leukemic B cells from death by apoptosis and upregulates Bcl-2 expression. J Exp Med. 1992 Nov. 1; 176(5):1319-26.

KLEIN, A., Miera, O., Bauer, O., Golfier, S., Schriever. F.; Chemosensitivity of 8 cell chronic lyrnphocytic leukemia and correlated expression of proteins regulating apoptosis, cell cycle and DNA repair; Leukemia. 2000 14.40-46.

PISTOIA, V.: Production of cytokines by human B cells in health and disease. Immunol Today. 1997 18:343-346.

TANGYE, S. G, Weston, K. M., Raison, R. L.; Interleukin-10 Inhibits the In vitro Proliferation of Human Activated Leukemic CD5+ B-cells; Leukemia and Lymphoma. 1999 30: 121-130.

PESCOVITZ, M. D. Rituximab, an Anti-CD20 Monoclonal Antibody: History and Mechanism of Action. Am J. Transpl. 2006 (6): 859-866.

REFF M. E., Garner K., Chambers K. S., Chinn P. C., Leonard J. E., Raab R., Newman R. A., Hanna N., Anderson D. R. Depletion of B cells in vivo by a chimeric mouse human monoclonal antibody to CD20. Blood. 1994 Jan. 15; 83(2):435-45.

PATHAN, N. I., Chu P., Hariharan K., Cheney C., Molina A., Byrd J. Mediation of apoptosis by and antitumour activity of lumiliximab in chronic lymphocytic leukemia cells and CD23+ lymphoma cell lines. Blood. 2008 Feb. 1; 111(3): 1594-602.

SOKOLOSKI, J A, et al. Antisense oligonucleotides to the p65 subunit of NF-kB block CD11 b expression and alter adhesion properties of differentiated HL-60 granulocytes. Blood. 15 Jul. 1993, vol. 82, no. 2, p. 625-632.

GURSEL, et al. Differential and competitive activation of human immune cells by distinct classes of CpG oligodeoxynucleotide. J Leuk Biol. 2002, vol. 71, p. 813-820.

JAHRSDORFER, et al. CpG DNA increases primary malignant B cell expression of costimulatory molecules and target antigens. J Leuk Biol. 2001, vol. 69, p. 81-88.

JAHRSDORFER, et al. B-cell lymhomas differ in their responsiveness to CpG oligodeoxynucleotides. Clin Can Res. 2005, vol. 11, p. 1490-1499.

JAHRSDORFER, et al. Immunostimulatory oligodeoxynucleotides induce apoptosis of B cell chronic lymphocytic leukemia cells. J Leuk Biol. 2005, vol. 77, p. 378-387.

---

The invention claimed is:

1. A method for reducing tumor growth of a lymphoma tumor in a patient in need thereof, comprising subcutaneously administering to the lymphoma tumor in said patient an isolated oligonucleotide sequence selected from the group consisting of the oligonucleotide sequences of SEQ ID NO 3, 1 and 4, wherein the tumor growth is reduced and wherein the isolated oligonucleotide sequence consists of SEQ ID NO 3, 1 or 4.

2. The method according to claim 1, wherein at least one nucleotide has a phosphate backbone modification.

3. The method according to claim 1, wherein said oligonucleotide is administered in a dose effective to elicit the expression of at least one of the cell surface markers CD20, CD40, CD54, CD69, CD80, and CD86.

4. The method according to claim 1, wherein the isolated oligonucleotide sequence consists of SEQ ID NO 1 or 4 and the oligonucleotide is administered in a dose effective to induce apoptosis.

5. The method according to claim 1, wherein said oligonucleotide is administered in a dose of about 1 to about 100 µg per kg body weight.

6. The method according to claim 1, wherein said oligonucleotide is administered before, after or essentially simultaneously with an anti-cancer treatment chosen from radiation treatment, hormone treatment, surgical intervention, chemotherapy, immunological therapies, photodynamic therapy, laser therapy, hyperthermia, cryotherapy, angiogenesis inhibition, or a combination of any of these.

7. The method according to claim 6, wherein said anti-cancer treatment is an immunological treatment and comprises the administration of an antibody to the patient.

8. The method according to claim 6, wherein said anti-cancer treatment is an immunological treatment which comprises the administration of an antibody to the patient, and said method involves the up-regulation of the expression of the cell surface marker CD20 prior to the administration of an antibody to the patient.

9. An isolated oligonucleotide sequence selected from the group consisting of the oligonucleotide sequences of SEQ ID NO 3, 1, 4, 5, 8, and 9, wherein the isolated oligonucleotide sequence consists of SEQ ID NO 3, 1, 4, 5, 8 or 9.

10. The isolated oligonucleotide sequence according to claim 9, wherein at least one nucleotide has a phosphate backbone modification.

11. The isolated oligonucleotide sequence according to claim 9, consisting of the oligonucleotide sequence of SEQ ID NO 3.

12. The isolated oligonucleotide sequence according to claim 9, consisting of the oligonucleotide sequence of SEQ ID NO 1.

13. The isolated oligonucleotide sequence according to claim 9, consisting of the oligonucleotide sequence of SEQ ID NO 4.

14. The isolated oligonucleotide sequence according to claim 9, consisting of the oligonucleotide sequence of SEQ ID NO 5.

15. The isolated oligonucleotide sequence according to claim 9, consisting of the oligonucleotide sequence of SEQ ID NO 8.

16. The isolated oligonucleotide sequence according to claim 9, consisting of the oligonucleotide sequence of SEQ ID NO 9.

* * * * *

SEQUENCE LISTING

```
<160> NUMBER OF SEQ ID NOS: 9

<210> SEQ ID NO 1
<211> LENGTH: 23
<212> TYPE: DNA
<213> ORGANISM: Artificial
<220> FEATURE:
<223> OTHER INFORMATION: Synthetic oligonucleotide

<400> SEQUENCE: 1
ccggggtcgc agctgagccc acg                                         23

<210> SEQ ID NO 2
<211> LENGTH: 21
<212> TYPE: DNA
<213> ORGANISM: Artificial
<220> FEATURE:
<223> OTHER INFORMATION: Synthetic oligonucleotide

<400> SEQUENCE: 2
atcgtctgcc atggtgaaga t                                           21

<210> SEQ ID NO 3
<211> LENGTH: 22
<212> TYPE: DNA
<213> ORGANISM: Artificial
<220> FEATURE:
<223> OTHER INFORMATION: Synthetic oligonucleotide

<400> SEQUENCE: 3
tcgtcgttct gccatcgtcg tt                                          22
```

```
<210> SEQ ID NO 4
<211> LENGTH: 14
<212> TYPE: DNA
<213> ORGANISM: Artificial
<220> FEATURE:
<223> OTHER INFORMATION: Synthetic oligonucleotide

<400> SEQUENCE: 4
ggggtcgtct gcgg                                                          14

<210> SEQ ID NO 5
<211> LENGTH: 16
<212> TYPE: DNA
<213> ORGANISM: Artificial
<220> FEATURE:
<223> OTHER INFORMATION: Synthetic oligonucleotide

<400> SEQUENCE: 5
gatcgtccgt cggggg                                                        16

<210> SEQ ID NO 6
<211> LENGTH: 19
<212> TYPE: DNA
<213> ORGANISM: Artificial
<220> FEATURE:
<223> OTHER INFORMATION: Synthetic oligonucleotide
<300> PUBLICATION INFORMATION:
<302> TITLE: Suppression of nuclear factor-kB dependent processes using
      oligonucleotides
<310> PATENT DOCUMENT NUMBER: US 6,498,147
<311> PATENT FILING DATE: 1993-08-20
<312> PUBLICATION DATE: 2002-01-17

<400> SEQUENCE: 6
ggaacagttc gtccatggc                                                     19

<210> SEQ ID NO 7
<211> LENGTH: 21
<212> TYPE: DNA
<213> ORGANISM: Artificial
<220> FEATURE:
<223> OTHER INFORMATION: Synthetic oligonucleotide
<300> PUBLICATION INFORMATION:
<301> AUTHORS: Sokoloski, J. et al.
<302> TITLE: Antisense oligonucleotides to the p65 subunit of NF-kB
      block CD11b expression and alter adhesion properties of
      differentiated HL-60 granulocytes
<303> JOURNAL: Blood
<304> VOLUME: 82
<305> ISSUE: 2
<306> PAGES: 625-632
<307> DATE: 1993-07-01

<400> SEQUENCE: 7
ggggaacagt tcgtccatgg c                                                  21

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide

<400> SEQUENCE: 8
tcgtcgttcg gccgatcgtc c                                                  21

<210> SEQ ID NO 9
<211> LENGTH: 21
```

```
<212> TYPE: DNA
<213> ORGANISM: Artificial
<220> FEATURE:
<223> OTHER INFORMATION: Synthetic oligonucleotide

<400> SEQUENCE: 9
tcgttcgtct gcttgttcgt c                                             21
```